United States Patent
Ghazi et al.

(10) Patent No.: US 10,531,844 B1
(45) Date of Patent: Jan. 14, 2020

(54) NARROW BEAM CT USING A 3D FLUENCE MODULATION AND SCATTER SHIELD SYSTEM

(71) Applicant: Malcova LLC, Baltimore, MD (US)

(72) Inventors: Peymon Mirsaeid Ghazi, Baltimore, MD (US); Tara Renee Ghazi, Baltimore, MD (US)

(73) Assignee: MALCOVA LLC, Baltimore, MD (US)

( * ) Notice: Subject to any disclaimer, the term of this patent is extended or adjusted under 35 U.S.C. 154(b) by 0 days.

(21) Appl. No.: 16/537,283

(22) Filed: Aug. 9, 2019

(51) Int. Cl.
  A61B 6/00 (2006.01)
  A61B 6/10 (2006.01)
  A61B 6/03 (2006.01)

(52) U.S. Cl.
  CPC .............. A61B 6/107 (2013.01); A61B 6/032 (2013.01); A61B 6/4435 (2013.01)

(58) Field of Classification Search
  None
  See application file for complete search history.

(56) References Cited

U.S. PATENT DOCUMENTS

| | | | |
|---|---|---|---|
| 4,145,610 A * | 3/1979 | Perilhou | A61B 6/032 378/19 |
| 4,315,146 A * | 2/1982 | Rudin | G21K 1/025 378/146 |
| 4,975,933 A | 12/1990 | Hampel | |
| 6,438,210 B1 | 8/2002 | Castleberry | |
| 6,744,852 B2 | 6/2004 | Klotz et al. | |
| 6,990,171 B2 | 1/2006 | Toth et al. | |
| 7,088,799 B2 | 8/2006 | Hoffman | |
| 8,199,883 B2 | 6/2012 | Arenson et al. | |
| 8,325,879 B2 | 12/2012 | Loos et al. | |
| 9,392,984 B2 | 7/2016 | Pelc et al. | |
| 2005/0013411 A1 | 1/2005 | Yahata et al. | |
| 2015/0279496 A1 * | 10/2015 | Bauer | A61B 6/032 378/19 |
| 2016/0035450 A1 * | 2/2016 | Date | G21K 1/067 378/36 |
| 2018/0317867 A1 | 11/2018 | Boone et al. | |

* cited by examiner

*Primary Examiner* — Hoon K Song
(74) *Attorney, Agent, or Firm* — Wilson Sonsini Goodrich & Rosati

(57) ABSTRACT

Described are apparatus and methods of operation for three dimensional fluence modulation and scatter shielding for dedicated computed tomography (CT). Through the disclosed invention, the number of incident photons on the field of view (FOV) of the imaging system becomes proportional to the path length of the photon through the anatomy of interest. The apparatus is comprises a patient specific x-ray fluence modulation unit and a scatter shield unit. The fluence modulation unit reduces radiation dose differences across the anatomical part and the dynamic range requirements for the x-ray detector. The scatter shield unit is intended for preventing the scattered beams from reaching the x-ray detector. The internal structures of each unit are composed of elements with adjustable positions dependent on the specific shape of the object in the field-of-view (FOV). Method of operation are also provided.

30 Claims, 24 Drawing Sheets

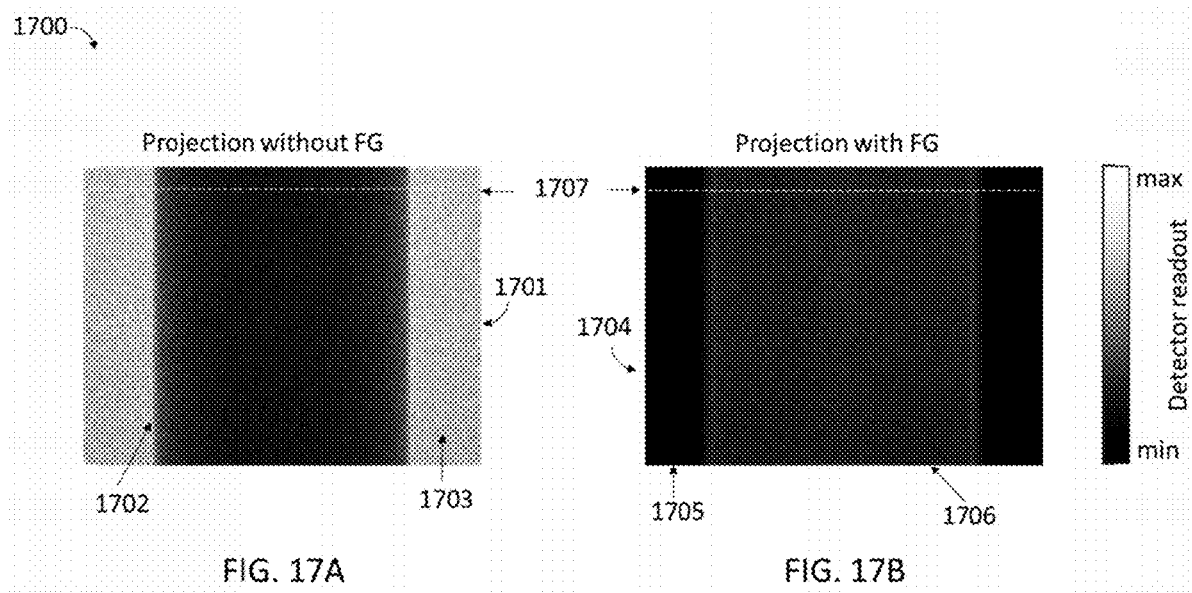
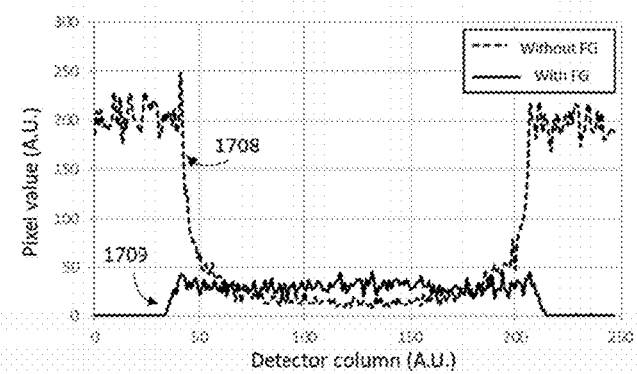
FIG. 17A  FIG. 17B
FIG. 17C

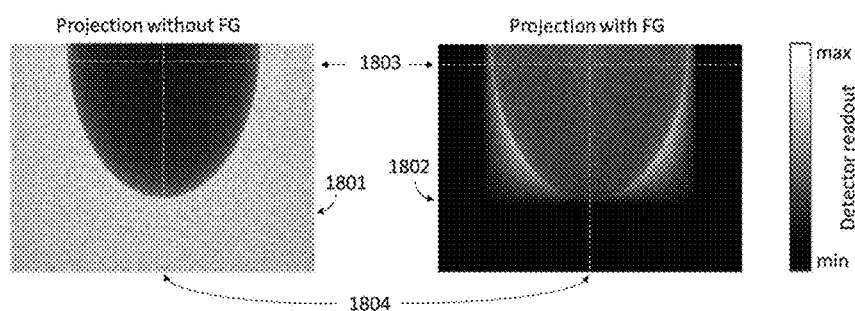
FIG. 18A
FIG. 18B
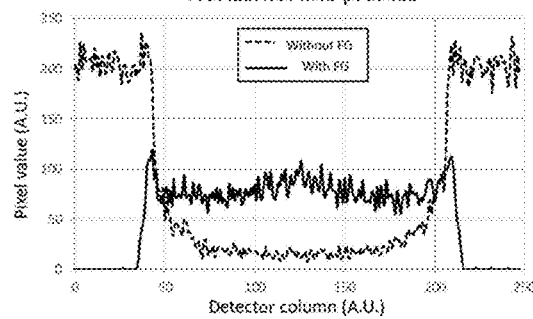
FIG. 18C
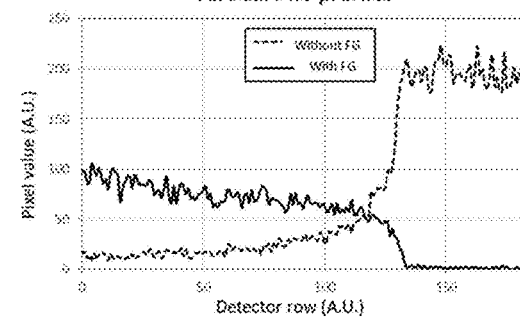
FIG. 18D

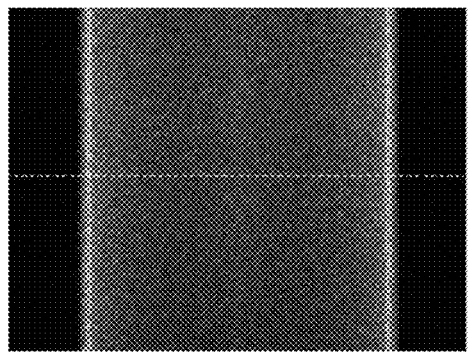 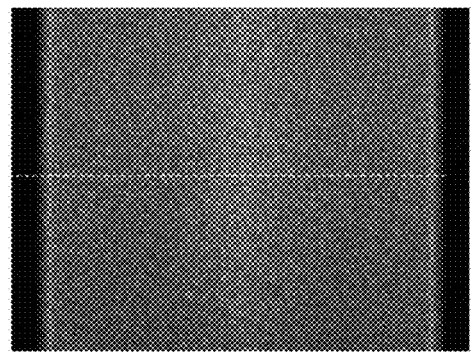
FIG. 23A    2301    FIG. 23B
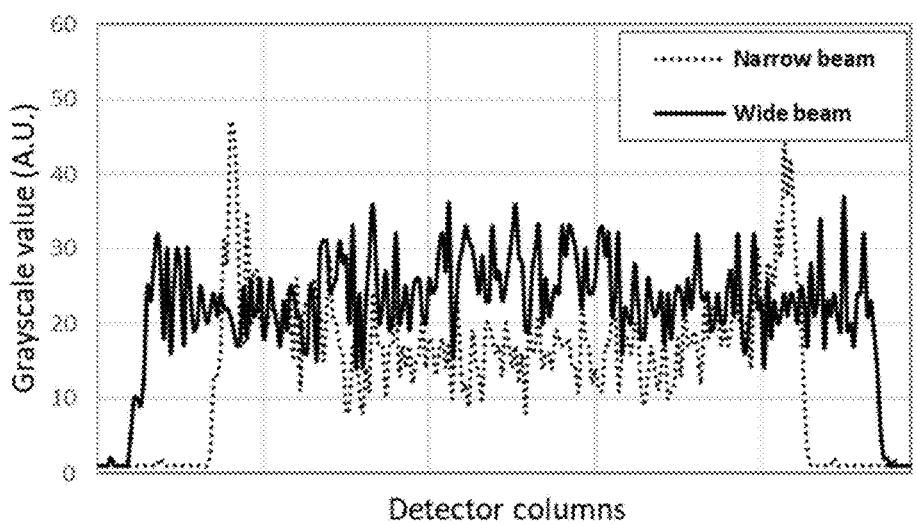
FIG. 23C

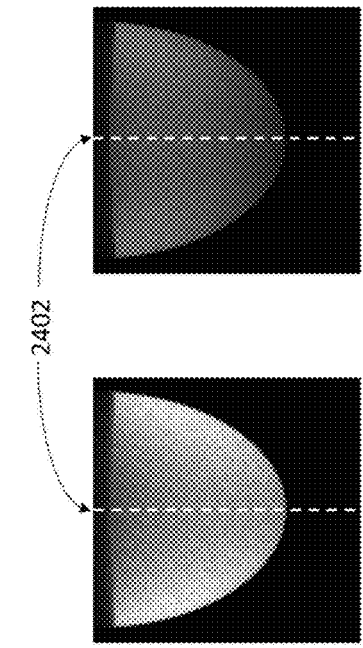
FIG. 24A
FIG. 24B
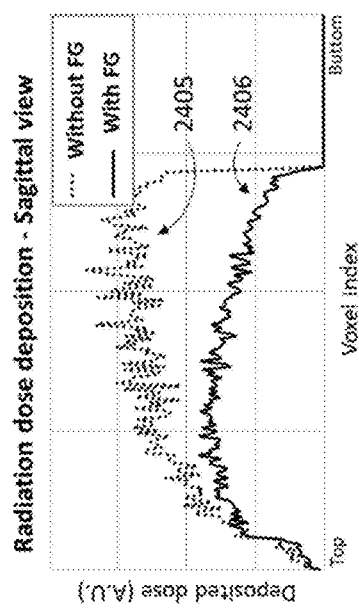
FIG. 24C
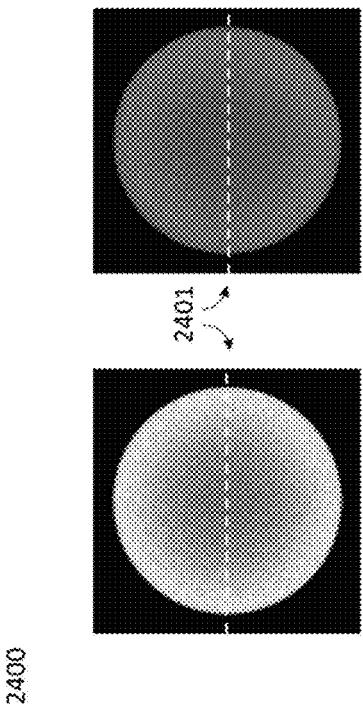
FIG. 24D
FIG. 24E
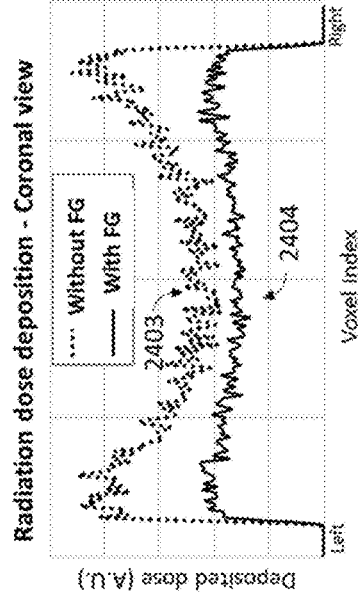
FIG. 24F

NARROW BEAM CT USING A 3D FLUENCE MODULATION AND SCATTER SHIELD SYSTEM

BACKGROUND

Radiologic computed tomography (CT) is a modality of imaging the internal areas of the human body using x-ray equipment, special image acquisition techniques and image reconstruction methods. A class of CT systems—dedicated CT systems—is designed to scan a specific anatomy such as the extremities, the head, and the female breast.

SUMMARY

We focus herein on the usage of dedicated CT to obtain images of anatomical extremities or specific organs such as the brain or breast. In the absence of a beam modulation technique, conventional CT systems emit a homogenous x-ray stream during an image acquisition without any modulation that accounts for the particularities and features of the anatomy. The breast or brain, for instance, are not uniform in shape, but rather exhibit contour and diametrical differences throughout their volume. These anatomical differences alter the path length of the emitted x-rays that are acquired by the CT system's detector.

When the x-ray fluence across the anatomy of interest is near-uniformly distributed, the detector elements that are along the attenuation profiles of the central parts of the anatomy receive much lower x-ray fluence compared to the peripheral parts. As a result, detector elements along the path of the photons transitioning through the peripheral regions are overexposed, while those along the path of the photons transitioning through the central regions of the organ are underexposed. Three main consequences arise from over- and underexposure: (1) unnecessarily high radiation dose is introduced to the peripheral regions of the anatomy, (2) an increased level of scattered radiation is generated in the peripheral regions and acquired at the x-ray detector which negatively impacts the contrast resolution of the reconstructed image, and (3) the risk of detector saturation caused by unattenuated or minimally-attenuated photons, or of the detected signal magnitude falling below the quantum noise threshold, increases. Each of these phenomena are discussed separately in the following.

Dose Deposited to the Anatomy

The radiation dose delivered in a body part depends on its size, shape and the structural distribution. For example, extremities such as arms and legs can be generally modelled as cylinders containing soft tissue and bony structures. In this case, the bony structure is mostly located near the central axis of the imaginary cylinder that encompasses the extremity. Bone tissue is made up of cell types that tend to be relatively high attenuators of x-rays. In order to obtain a high-quality tomographic image of an internal structure of a bone, therefore, a higher number of penetrating x-rays is required than would be for imaging a similarly sized region of soft tissue, for example. When a uniform x-ray beam is utilized for an extremity, therefore, the high x-ray fluence required to traverse through bone is applied to all regions of the extremity. This leads to introducing high levels of radiation dose to the regions close to the peripheral parts of the extremity.

In the case of the breast, entirely composed of soft tissue, similar issues occur, but for different anatomical reasons. Though the breast is often modelled as a cylinder in dedicated breast CT, the breast region nearer the chest wall is typically larger in diameter than the region nearest the nipple. Exposing a pendent breast to an almost uniformly distributed x-ray beam results in an increased anterior absorbed dose, in regions near the nipple, relative to the posterior regions of the breast. Additionally, the outermost soft tissue nearest the skin is exposed to greater dose compared to more medial regions.

FIGS. 1A-1D provide a visual representation of the deposited dose in a simulated breast modelled as a homogenous, half-ellipsoidal phantom. Coronal (FIG. 1A) and sagittal (FIG. 1C) views are shown. The associated profiles along the horizontal 101 and vertical 102 lines are respectively displayed in FIGS. 1B and 1D, illustrating that the deposited dose is highly varying throughout the breast.

Acquisition of Scattered Photons

X-ray overexposure generally leads to an increase in scattered radiation acquired by the x-ray detector. Detected scattered radiation negatively impacts the contrast resolution of the CT image. A simulation example of the received scattered signal at a flat panel detector is provided in FIGS. 2A-2C where the primary and scatter constituting components of a projection are separately shown in FIGS. 2A and 2B, respectively. The profiles across the horizontal lines 201 shown in FIGS. 2A-2B are displayed in FIG. 2C. Dividing the accumulated primary signal 202 by the corresponding scatter signal 203 yields the scatter-to-primary-ratio (SPR) 204. By observing the spatial variations of the acquired scattered signal in FIG. 2B, one will appreciate that the density of the acquired scattered photons is higher at the detector elements corresponding to the peripheral regions compared with central regions. Scattered radiation negatively influences image quality by introducing both low-frequency shading artifacts (commonly referred to as cupping artifact) and high-frequency loss in contrast resolution of microstructures (such as small ducts and microcalcifications in breast CT or auditory ossicle in head CT). Although low frequency impacts can be partially corrected by implementing post processing algorithms, correcting for the high frequency impacts of x-ray scatter is a difficult task due to the stochastic nature of x-ray scatter phenomenon. Therefore, the most optimal strategy in managing scatter is to avoid recording it during the image acquisition. Such scatter management solutions are generally referred to as the scatter rejection techniques.

Detector's Dynamic Range

The readout signal of the employed detector technology in the design of a CT system is bound by its dynamic range. In detector technology, dynamic range is always limited to an extent. A limited dynamic range can lead to data overflow at the detector elements that receive unattenuated or minimally attenuated rays. At low levels of detected x-ray quanta, a limited dynamic range can result in subpar differentiations between signal level and inherent quantum noise of a CT image. A series of visual representations 300 for body parts with different shapes are provided in FIGS. 3A-3E. FIG. 3A shows a cross section 301 of the object placed in the FOV of a CT scanner. The object is assumed to have an elliptical cross section, placed between an x-ray tube 302 and an x-ray detector 303. Variations in the path length and the received signal along both fan and cone angles depend on the shape and tissue distribution of the anatomical part. In the case displayed in FIG. 3A, the received path length 304 of the x-ray beam is minimal at the detector elements on the path of the vertices of the ellipse and maximal at the center. The recorded signal 305 is inversely proportional to the path length 304. In dedicated extremities CT scanners, arms or legs can be modelled reasonably well as cylinders (FIG. 3B).

In dedicated breast CT scanners, a pendent breast can be modelled as half-ellipsoid (FIG. 3C). In a CT head imaging system, the skull case can be modelled as a prolate semi-spheroid (FIG. 3D) or prolate spheroid (FIG. 3E). As illustrated in each example, both path lengths and received signal vary along the cone angle.

The diagnostic value of a CT system is improved by resolving the non-uniformities in the detected signal and reducing the acquisition of the scattered photons. Moreover, an objective of a design optimization solutions for x-ray imaging is lowering the radiation dose introduced to patient.

In conventional computed tomography, these strategies in addressing the issues stated above commonly involve the design of pieces of hardware incorporating x-ray attenuating filters placed between the x-ray source and the object.

Bowtie-shaped filters are commonly used in multidetector CT scanners. The general assumption in designing the bowtie filters is that the object in the field of view of scanner, whether it is the whole patient body or a specific part of the body, has an elliptical tube shape. This may be the case in imaging extremities, where an extended arm or leg may be represented by a cylinder with an acceptable error tolerance, but in the case of the brain or the breast where the diameter of the enclosing cylinder reduces towards the sides, utilizing the bowtie results in overexposing the tapered parts of the organ to x-rays.

Feedback filters are typically implemented through design of a feedback-controlled beam modulation. In these cases, the physical structure of the filter is modified per feedback gained from the signal received in detector. Drawbacks of these designs include prolonged scan time, artifacts arising from misregistration between the actual anatomical structure and the received feedback signal and the increased patient dosage due to suboptimal adjustments in the filter.

Organ-specific adaptive filters are developed to subset the general shape and size of the anatomy of interest into groupings, with specific filters then designed for each group. Employing organ-specific filters, compared to other filters, requires an extra step of finding the closest filter size to fit the specific size of a patient. Several drawbacks exist in the usage of organ-specific adaptive filters. First, there is the possibility that an inaccurate grouping or categorization of a specific patient's anatomy is made. This may occur in cases where assignation of a group is determined based on the pre-existing molds the organ best fits to. Some error in the fit between mold and anatomy is tolerated in this technique. If the error is an overestimation of the size of the anatomical part, this will lead to an overexposure of the anatomy during a scan procedure. Underestimation, on the other hand, can cause patient discomfort and inadequate x-ray coverage of the organ during image acquisition.

A flexibility in designing beam modulation filters is provided through dynamic attenuators. With this approach, the number of photons incident on the object in any ray can be adjusted according to the internal composition of the body part placed in FOV. This solution's drawbacks relate mainly to the difficulties in implementing a proper operation. The slight deviation from the optimal mechanical operation in this class of beam modulators can lead to introducing severe imaging artifacts.

Scatter contamination reduces the observed contrast resolution observed in projections. The compound scatter accumulation in projections can be reduced by simply increasing the gap between the x-ray detector and the object placed in scanner's FOV; however, this approach may decrease the coverage and increase the focal spot blur, thereby, reduce the spatial resolution of the imaging system. Another option is the usage of anti-scatter grids. However, the dose penalty in using a grid system for low dose x-ray imaging applications, such as dedicated breast CT, as well as the technical difficulties in correcting for the septal shadow in the projections render this option prohibitive.

The limitations of existing beam modulation filters and scatter rejection solutions discussed above are overcome by the present invention. Described is a patient-specific apparatus composed of a dynamic Fluence Gate (FG) unit, a Scatter Shield (SS) unit, and the corresponding methods of, and for, operation in dedicated CT systems. When the apparatus is implemented within a CT system, the fluence received on the detector panel is almost entirely composed of primary photons and can be modulated along the fan and cone angles in accordance with the characteristic attenuation properties of the body part placed in FOV of the imaging system. The entire assembly of the present invention is referred to hereinafter as the Fluence Gate—Scatter Shield (FG-SS) apparatus.

The fluence modulation technique presented in this invention is achieved by continually changing the collimation of the total span of the sourced photons as the FG drum rotates. As described above, the prior approaches and inventions, have applied filtering to a portion of the beam. Dynamic collimation as presented herein is a novel approach to fluence modulation within a CT system.

According to various embodiments, the FG unit is a dynamic collimator assembly composed of a rotating drum (referred to herein after as the FG drum), on top of which are installed two sheets of high x-ray attenuating material (referred to herein after as the FG sheets), a sensory system and the constituent robotics. The FG unit is positioned between the x-ray source and the anatomy of interest. The sheets are positioned such that a narrow gap (referred to herein after as the FG window) is created between them. Nearly the entire beam generated at the sources is stopped by the FG sheets, except a narrow beam that escapes through the FG window. The size of the FG window can be modulated prior to or during a scan procedure via robotics attached to each sheet. To form a projection, the FG drum rotates circularly to allow its window to sweep the entire span of the fan angle covering the entire FOV. The resulting narrow beam is projected on the anatomy of interest and the detector panel.

According to various embodiments, the SS unit is an assembly, referred to herein after as the SS unit, rotating around the FOV composed of a rotating drum (referred to herein after as the SS drum), on top of which are installed two sheets of high x-ray attenuating material (referred to herein after as the SS sheets), a sensory system and the constituent robotics. These sheets are positioned such that a gap (referred to herein after as the SS window) is created through which the narrow beam that has transitioned through the object and almost entirely composed of the primary photons, traverses to reach the detector panel. To form a projection, the SS drum rotates circularly to allow the SS window to sweep the entire fan angle coverage of the FOV.

In yet another embodiment of this invention, the circular motions of the drums of the FG and SS units are synchronized such that the photons within the resulting narrow beam from the FG unit can traverse through the FOV and SS window and reach the detector. Described is a control system that uses a plurality of sensors to adjust and synchronize these motions.

In one aspect, disclosed herein are radiologic computed tomography (CT) systems comprising: a gantry configured to rotate on a first axis of rotation to allow the CT system to capture a plurality of projections of a target; a x-ray source affixed to the gantry and configured to generate a beam of x-ray photons; a x-ray detector affixed to the gantry; a robotic fluence gate system affixed to the gantry between the x-ray source and the x-ray detector and comprising a rotational platform configured to rotate on a second axis of rotation and a plurality of fluence modulation sheets forming a fluence gate window, the fluence gate system configured to modulate a fluence of the beam of x-ray photons; a robotic scatter shield system affixed to the gantry between the x-ray source and the x-ray detector and comprising a rotational platform configured to rotate on a third axis of rotation and a plurality of scatter shield sheets forming a scatter shield window, the scatter shield system configured to shield scattered x-ray photons from the x-ray detector; and a controller configured to perform at least: synchronize a speed and a phase of rotation of the gantry, the fluence gate system, and the scatter shield system to maintain a line-of-sight from the x-ray source to the x-ray detector during capture of each projection of the target; activate the x-ray source when the line-of-sight is open; and deactivate the x-ray source when the line-of-sight is closed. In some embodiments, one or more of: the x-ray source, the fluence gate system, the x-ray detector, and the scatter shield system are affixed directly to the gantry. In some embodiments, one or more of: the x-ray source, the fluence gate system, the x-ray detector, and the scatter shield system are affixed indirectly to the gantry. In some embodiments, the fluence gate system comprises two fluence modulation sheets. In some embodiments, the fluence modulation sheets comprise an x-ray attention material. In some embodiments, the fluence modulation sheets are substantially flat. In other embodiments, the fluence modulation sheets are curved. In some embodiments, the fluence gate system comprises robotics configured to position each fluence modulation sheet in each of four axes of adjustment to change a size, a shape, or both a size and a shape of the fluence gate window. In further embodiments, the fluence gate system comprises one or more sensors configured to generate data used to inform the positioning of each fluence modulation sheet. In further embodiments, the controller is further configured to instruct the robotics of the fluence gate system to position each fluence modulation sheet for each projection of the target. In some embodiments, the scatter shield system comprises two fluence modulation sheets. In some embodiments, the scatter shield sheets comprise an x-ray attention material. In some embodiments, the scatter shield sheets are substantially flat. In other embodiments, the scatter shield sheets are curved. In some embodiments, the scatter shield system comprises robotics configured to position each scatter shield sheet in each of four axes of adjustment to change a size, a shape, or both a size and a shape of the scatter shield window. In further embodiments, the scatter shield system comprises one or more sensors configured to generate data used to inform the positioning of each scatter shield sheet. In further embodiments, the controller is further configured to instruct the robotics of the scatter shield system to position each scatter shield sheet for each projection of the target. In some embodiments, the first axis of rotation, the second axis of rotation, and the third axis of rotation are substantially parallel. In some embodiments, the beam of x-ray photons incident on the x-ray detector is substantially scatter-free. In further embodiments, the beam of x-ray photons incident on the x-ray detector is scatter-free. In some embodiments, the target is an anatomical target. In further embodiments, the beam has a x-ray beam energy falling within a diagnostic range of 20 keV to 140 keV. In still further embodiments, the anatomical target is a human extremity. In other embodiments, the anatomical target is a human female breast. In yet other embodiments, the anatomical target is a whole human body.

In another aspect, disclosed herein are radiologic computed tomography (CT) systems comprising: a gantry configured to rotate on a first axis of rotation to allow the CT system to capture a plurality of projections of a target; a x-ray source affixed directly or indirectly to the gantry and configured to generate a beam of x-ray photons; a x-ray detector affixed directly or indirectly to the gantry; a robotic fluence gate system affixed directly or indirectly to the gantry between the x-ray source and the x-ray detector and comprising a rotational platform configured to rotate on a second axis of rotation and a plurality of fluence modulation sheets forming a fluence gate window, the fluence gate system configured to modulate a fluence of the beam of x-ray photons; and a controller configured to perform at least: synchronize a speed and a phase of rotation of the gantry and the fluence gate system to maintain a line-of-sight from the x-ray source to the x-ray detector during capture of each projection of the target; activate the x-ray source when the line-of-sight is open; and deactivate the x-ray source when the line-of-sight is closed. In some embodiments, one or more of: the x-ray source, the fluence gate system, and the x-ray detector are affixed directly to the gantry. In some embodiments, one or more of: the x-ray source, the fluence gate system, and the x-ray detector are affixed indirectly to the gantry. In some embodiments, the fluence gate system comprises two fluence modulation sheets. In some embodiments, the fluence modulation sheets comprise an x-ray attention material. In some embodiments, the fluence modulation sheets are substantially flat. In other embodiments, the fluence modulation sheets are curved. In some embodiments, the fluence gate system comprises robotics configured to position each fluence modulation sheet in each of four axes of adjustment to change a size, a shape, or both a size and a shape of the fluence gate window. In further embodiments, the fluence gate system comprises one or more sensors configured to generate data used to inform the positioning of each fluence modulation sheet. In further embodiments, the controller is further configured to instruct the robotics of the fluence gate system to position each fluence modulation sheet for each projection of the target. In some embodiments, the first axis of rotation and the second axis of rotation are substantially parallel. In some embodiments, the beam of x-ray photons incident on the x-ray detector is substantially scatter-free. In further embodiments, the beam of x-ray photons incident on the x-ray detector is scatter-free. In some embodiments, the target is an anatomical target. In further embodiments, the beam has a x-ray beam energy falling within a diagnostic range of 20 keV to 140 keV. In still further embodiments, the anatomical target is a human extremity, a human female breast, or a whole human body.

In another aspect, disclosed herein are radiologic computed tomography (CT) systems comprising: a gantry configured to rotate on a first axis of rotation to allow the CT system to capture a plurality of projections of a target; a x-ray source affixed directly or indirectly to the gantry and configured to generate a beam of x-ray photons; a x-ray detector affixed directly or indirectly to the gantry; a robotic scatter shield system affixed directly or indirectly to the gantry between the x-ray source and the x-ray detector and comprising a rotational platform configured to rotate on a second axis of rotation and a plurality of scatter shield sheets forming a scatter shield window, the scatter shield system configured to shield scattered x-ray photons from the x-ray detector; and a controller configured to perform at least: synchronize a speed and a phase of rotation of the gantry, the fluence gate system, and the scatter shield system to maintain a line-of-sight from the x-ray source to the x-ray detector during capture of each projection of the target; activate the x-ray source when the line-of-sight is open; and deactivate the x-ray source when the line-of-sight is closed. In some embodiments, one or more of: the x-ray source, the x-ray detector, and the scatter shield system are affixed directly to the gantry. In some embodiments, one or more of: the x-ray source, the x-ray detector, and the scatter shield system are affixed indirectly to the gantry. In some embodiments, the scatter shield system comprises two fluence modulation sheets. In some embodiments, the scatter shield sheets comprise an x-ray attention material. In some embodiments, the scatter shield sheets are substantially flat. In other embodiments, the scatter shield sheets are curved. In some embodiments, the scatter shield system comprises robotics configured to position each scatter shield sheet in each of four axes of adjustment to change a size, a shape, or both a size and a shape of the scatter shield window. In further embodiments, the scatter shield system comprises one or more sensors configured to generate data used to inform the positioning of each scatter shield sheet. In further embodiments, the controller is further configured to instruct the robotics of the scatter shield system to position each scatter shield sheet for each projection of the target. In some embodiments, the first axis of rotation and the second axis of rotation are substantially parallel. In some embodiments, the beam of x-ray photons incident on the x-ray detector is substantially scatter-free. In further embodiments, the beam of x-ray photons incident on the x-ray detector is scatter-free. In some embodiments, the target is an anatomical target. In further embodiments, the beam has a x-ray beam energy falling within a diagnostic range of 20 keV to 140 keV. In still further embodiments, the anatomical target is a human extremity, a human female breast, or a whole human body.

In another aspect, disclosed herein are methods of performing radiologic computed tomography (CT) to capture a plurality of projections of a target, the method comprising: generating, by a x-ray source affixed to a gantry, a beam of x-ray photons; controlling, by a controller unit, at least the following: speed and phase of rotation of a robotic fluence gate system affixed to the gantry between the x-ray source and a x-ray detector to maintain a line-of-sight from the x-ray source to the x-ray detector during capture of each projection of the target, the fluence gate system comprising a rotational platform and a plurality of fluence modulation sheets forming a fluence gate window, the fluence gate system configured to modulate a fluence of the beam of x-ray photons; speed and phase of rotation of a robotic scatter shield system affixed to the gantry between the x-ray source and the x-ray detector to maintain a line-of-sight from the x-ray source to the x-ray detector during capture of each projection of the target, the scatter shield system comprising a rotational platform and a plurality of scatter shield sheets forming a scatter shield window, the scatter shield system configured to shield scattered x-ray photons from the x-ray detector; activation of the x-ray source when the line-of-sight is open; and deactivation of the x-ray source when the line-of-sight is closed; and detecting, by the x-ray detector affixed to the gantry, the beam of x-ray photons. In some embodiments, the fluence gate system further comprises robotics configured to position each fluence modulation sheet in each of four axes of adjustment to change a size, a shape, or both a size and a shape of the fluence gate window. In further embodiments, the fluence gate system further comprises one or more sensors configured to generate data used to inform the positioning of each fluence modulation sheet. In still further embodiments, the controller unit is further configured to instruct the robotics of the fluence gate system to position each fluence modulation sheet for each projection of the target. In some embodiments, the scatter shield system comprises robotics configured to position each scatter shield sheet in each of four axes of adjustment to change a size, a shape, or both a size and a shape of the scatter shield window. In further embodiments, the scatter shield system comprises one or more sensors configured to generate data used to inform the positioning of each scatter shield sheet. In still further embodiments, the controller unit is further configured to instruct the robotics of the scatter shield system to position each scatter shield sheet for each projection of the target.

BRIEF DESCRIPTION OF THE DRAWINGS

A better understanding of the features and advantages of the present subject matter will be obtained by reference to the following detailed description that sets forth illustrative embodiments and the accompanying drawings of which:

FIGS. 17A-17C illustrate simulation results for projections of a cylindrical phantom on a detector panel without and with utilization of the FG-SS apparatus in accordance with embodiments of the present subject matter, in addition to a comparison of a first line profile (without using FG) and a second line profile (using FG) through the simulated projection images along the horizontal dimension;

FIGS. 18A-18D illustrate simulation estimations of the detected signal without and with utilizing FG-SS apparatus in a dedicated breast CT system in accordance with embodiments of the invention, in addition to a comparison of a first line profile (without using FG-SS apparatus) and a second line profile (using FG-SS apparatus) through the simulated projection images along the horizontal and vertical dimensions;

FIGS. 23A-23C illustrate an exemplar comparison between the cylindrical phantom scans with and without a correction for the non-circular cross section of the phantom; and FIGS. 24A-24F show simulated distributions of the radiation dose in a homogenous breast phantom scanned on a CT system without and with utilization of the FG-SS apparatus.

DETAILED DESCRIPTION OF THE INVENTION

Figure 1A:
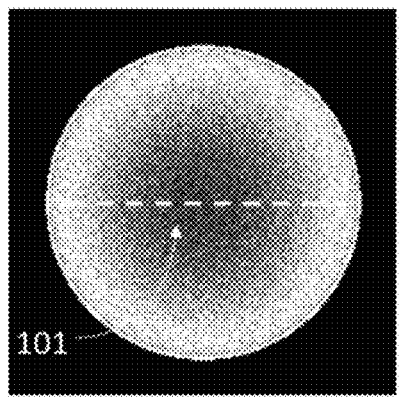
FIGS. 1A-lD show simulated distributions of the radiation dose in a homogenous breast phantom.
Figure 1B:
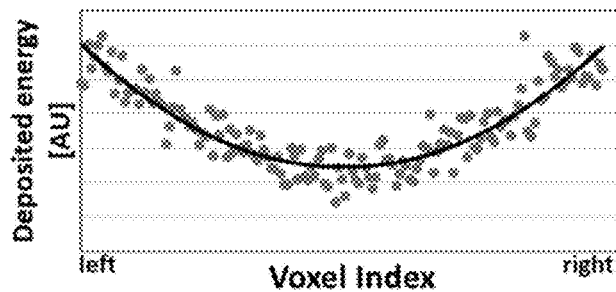
Figure 1C:
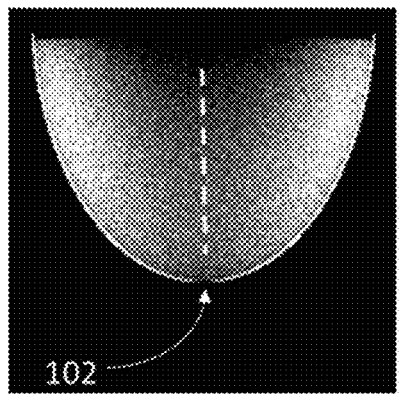
Figure 1D:
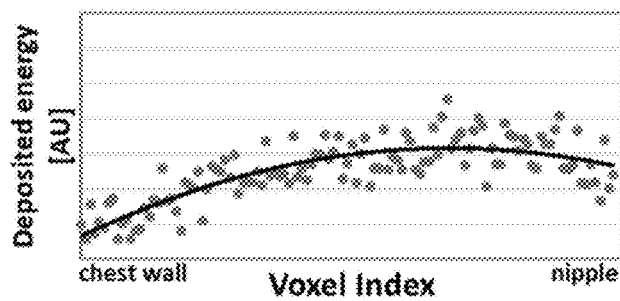
Figure 2C:
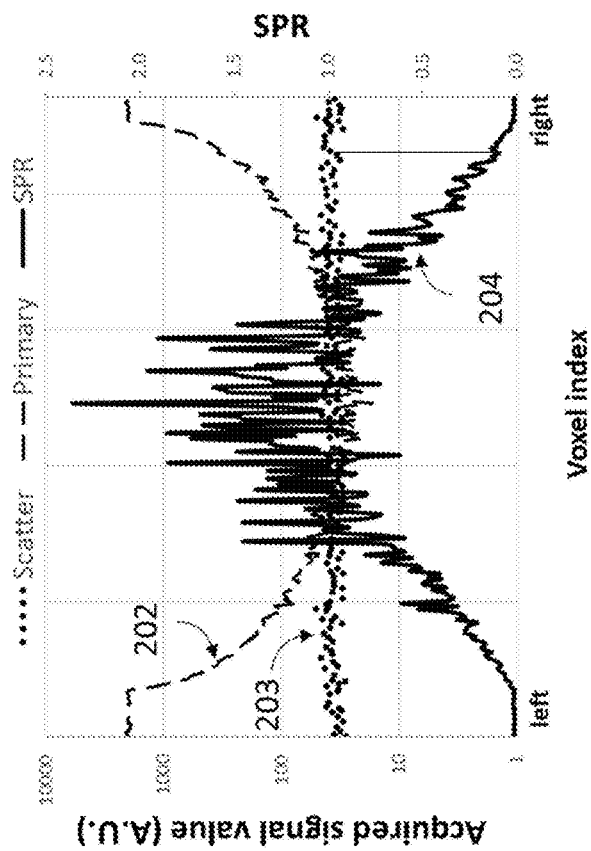
FIGS. 2A-2C show simulated distributions of the scattered photon distribution in projections of a homogenous breast phantom.
Figure 2A:
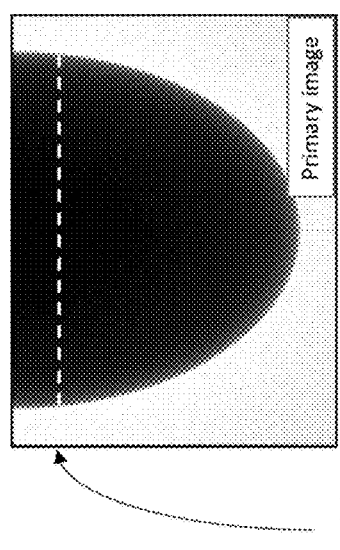
Figure 2B:
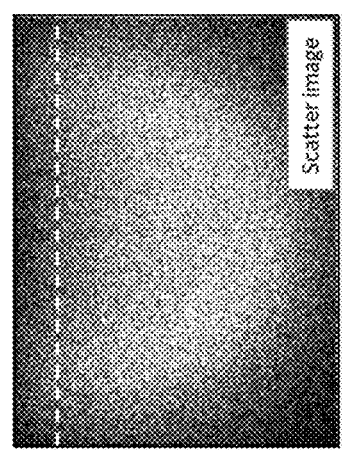
Figure 3A:
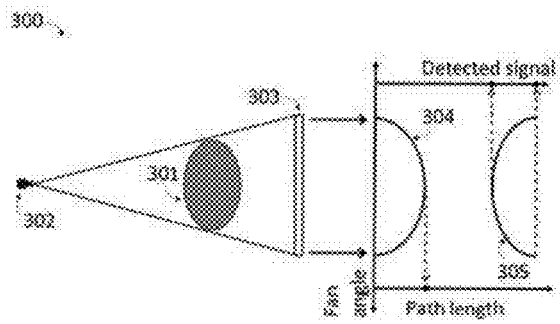
FIGS. 3A-3E show the total path length and the projection signal intensity in fan-beam and cone-beam geometries (different geometrical shapes represent different organs)
Figure 3B:
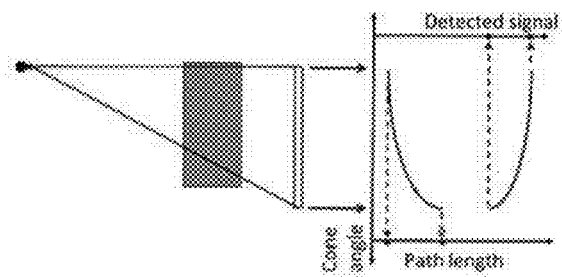
Figure 3C:
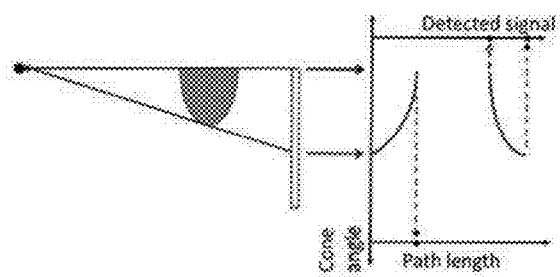
Figure 3D:
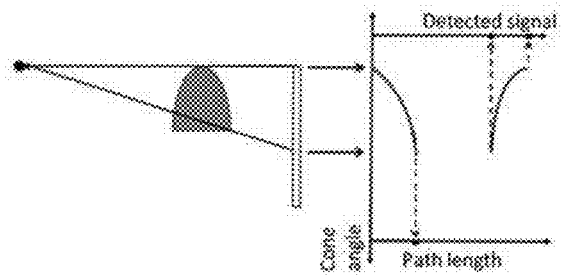
Figure 3E:
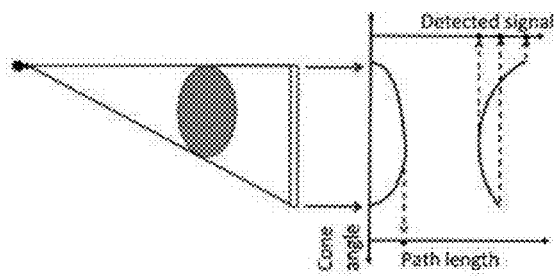

Described herein, in certain embodiments, are radiologic computed tomography (CT) systems comprising: a gantry configured to rotate on a first axis of rotation to allow the CT system to capture a plurality of projections of a target; a x-ray source affixed to the gantry and configured to generate a beam of x-ray photons; a x-ray detector affixed to the gantry; a robotic fluence gate system affixed to the gantry between the x-ray source and the x-ray detector and comprising a rotational platform configured to rotate on a second axis of rotation and a plurality of fluence modulation sheets forming a fluence gate window, the fluence gate system configured to modulate a fluence of the beam of x-ray photons; a robotic scatter shield system affixed to the gantry between the x-ray source and the x-ray detector and comprising a rotational platform configured to rotate on a third axis of rotation and a plurality of scatter shield sheets forming a scatter shield window, the scatter shield system configured to shield scattered x-ray photons from the x-ray detector; and a controller configured to perform at least: synchronize a speed and a phase of rotation of the gantry, the fluence gate system, and the scatter shield system to maintain a line-of-sight from the x-ray source to the x-ray detector during capture of each projection of the target; activate the x-ray source when the line-of-sight is open; and deactivate the x-ray source when the line-of-sight is closed. In some embodiments, one or more of: the x-ray source, the fluence gate system, the x-ray detector, and the scatter shield system are affixed directly to the gantry. In some embodiments, one or more of: the x-ray source, the fluence gate system, the x-ray detector, and the scatter shield system are affixed indirectly to the gantry. In some embodiments, the fluence gate system comprises two fluence modulation sheets. In some embodiments, the fluence modulation sheets comprise an x-ray attention material. In some embodiments, the fluence modulation sheets are substantially flat. In other embodiments, the fluence modulation sheets are curved. In some embodiments, the fluence gate system comprises robotics configured to position each fluence modulation sheet in each of four axes of adjustment to change a size, a shape, or both a size and a shape of the fluence gate window. In further embodiments, the fluence gate system comprises one or more sensors configured to generate data used to inform the positioning of each fluence modulation sheet. In further embodiments, the controller is further configured to instruct the robotics of the fluence gate system to position each fluence modulation sheet for each projection of the target. In some embodiments, the scatter shield system comprises two fluence modulation sheets. In some embodiments, the scatter shield sheets comprise an x-ray attention material. In some embodiments, the scatter shield sheets are substantially flat. In other embodiments, the scatter shield sheets are curved. In some embodiments, the scatter shield system comprises robotics configured to position each scatter shield sheet in each of four axes of adjustment to change a size, a shape, or both a size and a shape of the scatter shield window. In further embodiments, the scatter shield system comprises one or more sensors configured to generate data used to inform the positioning of each scatter shield sheet. In further embodiments, the controller is further configured to instruct the robotics of the scatter shield system to position each scatter shield sheet for each projection of the target. In some embodiments, the first axis of rotation, the second axis of rotation, and the third axis of rotation are substantially parallel. In some embodiments, the beam of x-ray photons incident on the x-ray detector is substantially scatter-free. In further embodiments, the beam of x-ray photons incident on the x-ray detector is scatter-free. In some embodiments, the target is an anatomical target. In further embodiments, the beam has a x-ray beam energy falling within a diagnostic range of 20 keV to 140 keV. In still further embodiments, the anatomical target is a human extremity. In other embodiments, the anatomical target is a human female breast. In yet other embodiments, the anatomical target is a whole human body.

Also described herein, in certain embodiments, are radiologic computed tomography (CT) systems comprising: a gantry configured to rotate on a first axis of rotation to allow the CT system to capture a plurality of projections of a target; a x-ray source affixed directly or indirectly to the gantry and configured to generate a beam of x-ray photons; a x-ray detector affixed directly or indirectly to the gantry; a robotic fluence gate system affixed directly or indirectly to the gantry between the x-ray source and the x-ray detector and comprising a rotational platform configured to rotate on a second axis of rotation and a plurality of fluence modulation sheets forming a fluence gate window, the fluence gate system configured to modulate a fluence of the beam of x-ray photons; and a controller configured to perform at least: synchronize a speed and a phase of rotation of the gantry and the fluence gate system to maintain a line-of-sight from the x-ray source to the x-ray detector during capture of each projection of the target; activate the x-ray source when the line-of-sight is open; and deactivate the x-ray source when the line-of-sight is closed. In some embodiments, one or more of: the x-ray source, the fluence gate system, and the x-ray detector are affixed directly to the gantry. In some embodiments, one or more of: the x-ray source, the fluence gate system, and the x-ray detector are affixed indirectly to the gantry. In some embodiments, the fluence gate system comprises two fluence modulation sheets. In some embodiments, the fluence modulation sheets comprise an x-ray attention material. In some embodiments, the fluence modulation sheets are substantially flat. In other embodiments, the fluence modulation sheets are curved. In some embodiments, the fluence gate system comprises robotics configured to position each fluence modulation sheet in each of four axes of adjustment to change a size, a shape, or both a size and a shape of the fluence gate window. In further embodiments, the fluence gate system comprises one or more sensors configured to generate data used to inform the positioning of each fluence modulation sheet. In further embodiments, the controller is further configured to instruct the robotics of the fluence gate system to position each fluence modulation sheet for each projection of the target. In some embodiments, the first axis of rotation and the second axis of rotation are substantially parallel. In some embodiments, the beam of x-ray photons incident on the x-ray detector is substantially scatter-free. In further embodiments, the beam of x-ray photons incident on the x-ray detector is scatter-free. In some embodiments, the target is an anatomical target. In further embodiments, the beam has a x-ray beam energy falling within a diagnostic range of 20 keV to 140 keV. In still further embodiments, the anatomical target is a human extremity, a human female breast, or a whole human body.

Also described herein, in certain embodiments, are radiologic computed tomography (CT) systems comprising: a gantry configured to rotate on a first axis of rotation to allow the CT system to capture a plurality of projections of a target; a x-ray source affixed directly or indirectly to the gantry and configured to generate a beam of x-ray photons; a x-ray detector affixed directly or indirectly to the gantry; a robotic scatter shield system affixed directly or indirectly to the gantry between the x-ray source and the x-ray detector and comprising a rotational platform configured to rotate on a second axis of rotation and a plurality of scatter shield sheets forming a scatter shield window, the scatter shield system configured to shield scattered x-ray photons from the x-ray detector; and a controller configured to perform at least: synchronize a speed and a phase of rotation of the gantry, the fluence gate system, and the scatter shield system to maintain a line-of-sight from the x-ray source to the x-ray detector during capture of each projection of the target; activate the x-ray source when the line-of-sight is open; and deactivate the x-ray source when the line-of-sight is closed. In some embodiments, one or more of: the x-ray source, the x-ray detector, and the scatter shield system are affixed directly to the gantry. In some embodiments, one or more of: the x-ray source, the x-ray detector, and the scatter shield system are affixed indirectly to the gantry. In some embodiments, the scatter shield system comprises two fluence modulation sheets. In some embodiments, the scatter shield sheets comprise an x-ray attention material. In some embodiments, the scatter shield sheets are substantially flat. In other embodiments, the scatter shield sheets are curved. In some embodiments, the scatter shield system comprises robotics configured to position each scatter shield sheet in each of four axes of adjustment to change a size, a shape, or both a size and a shape of the scatter shield window. In further embodiments, the scatter shield system comprises one or more sensors configured to generate data used to inform the positioning of each scatter shield sheet. In further embodiments, the controller is further configured to instruct the robotics of the scatter shield system to position each scatter shield sheet for each projection of the target. In some embodiments, the first axis of rotation and the second axis of rotation are substantially parallel. In some embodiments, the beam of x-ray photons incident on the x-ray detector is substantially scatter-free. In further embodiments, the beam of x-ray photons incident on the x-ray detector is scatter-free. In some embodiments, the target is an anatomical target. In further embodiments, the beam has a x-ray beam energy falling within a diagnostic range of 20 keV to 140 keV. In still further embodiments, the anatomical target is a human extremity, a human female breast, or a whole human body.

Also described herein, in certain embodiments, are methods of performing radiologic computed tomography (CT) to capture a plurality of projections of a target, the method comprising: generating, by a x-ray source affixed to a gantry, a beam of x-ray photons; controlling, by a controller unit, at least the following: speed and phase of rotation of a robotic fluence gate system affixed to the gantry between the x-ray source and a x-ray detector to maintain a line-of-sight from the x-ray source to the x-ray detector during capture of each projection of the target, the fluence gate system comprising a rotational platform and a plurality of fluence modulation sheets forming a fluence gate window, the fluence gate system configured to modulate a fluence of the beam of x-ray photons; speed and phase of rotation of a robotic scatter shield system affixed to the gantry between the x-ray source and the x-ray detector to maintain a line-of-sight from the x-ray source to the x-ray detector during capture of each projection of the target, the scatter shield system comprising a rotational platform and a plurality of scatter shield sheets forming a scatter shield window, the scatter shield system configured to shield scattered x-ray photons from the x-ray detector; activation of the x-ray source when the line-of-sight is open; and deactivation of the x-ray source when the line-of-sight is closed; and detecting, by the x-ray detector affixed to the gantry, the beam of x-ray photons. In some embodiments, the fluence gate system further comprises robotics configured to position each fluence modulation sheet in each of four axes of adjustment to change a size, a shape, or both a size and a shape of the fluence gate window. In further embodiments, the fluence gate system further comprises one or more sensors configured to generate data used to inform the positioning of each fluence modulation sheet. In still further embodiments, the controller unit is further configured to instruct the robotics of the fluence gate system to position each fluence modulation sheet for each projection of the target. In some embodiments, the scatter shield system comprises robotics configured to position each scatter shield sheet in each of four axes of adjustment to change a size, a shape, or both a size and a shape of the scatter shield window. In further embodiments, the scatter shield system comprises one or more sensors configured to generate data used to inform the positioning of each scatter shield sheet. In still further embodiments, the controller unit is further configured to instruct the robotics of the scatter shield system to position each scatter shield sheet for each projection of the target.

FG-SS Apparatus

Figure 4:
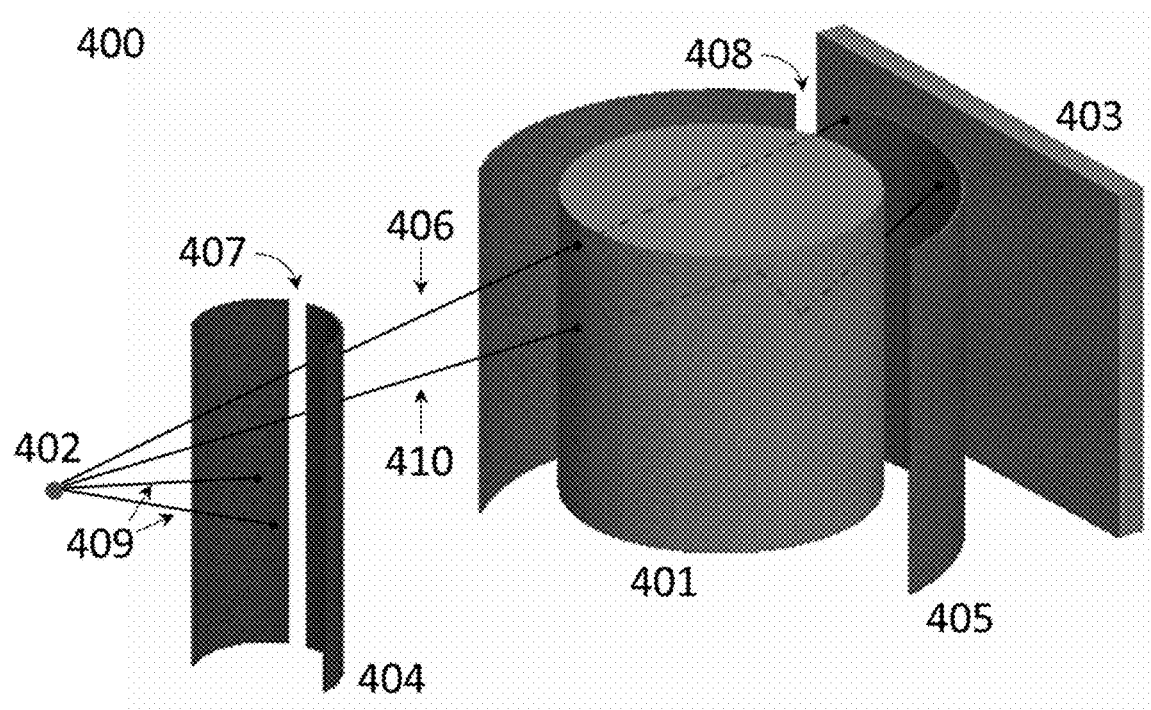
FIG. 4 is a perspective view that shows the configuration of a cone beam CT imaging system equipped with the FG-SS apparatus.

FIG. 4 illustrates a prospective view of an exemplar cone beam CT system 400. Here, a cylindrical anatomical part 401, such as an extremity, is positioned between an x-ray source 402 and an x-ray detector 403. The anatomical part may assume a semi-ellipsoidal shape such as a pendent breast, or a prolate spheroid such as a head. Two rotating physical structures are placed along the generated x-ray beam between the source and detector. The physical structure positioned immediately in front of the source along the x-ray beam, and rotating circularly, is the FG unit 404. SS unit 405 is a separate physical structure rotating around the FOV. The design and method of control of the drums within the units are such that an x-ray photon 406 received at the detector must transition through the FG window 407, the object of interest 401 and SS window 408. The x-ray photons 409 that are not aligned with the FG window are absorbed within the FG sheets. The x-ray photons 410 that pass through the FG window, but are scattered in the anatomy of interest, are absorbed within the SS sheets.

Figure 5:
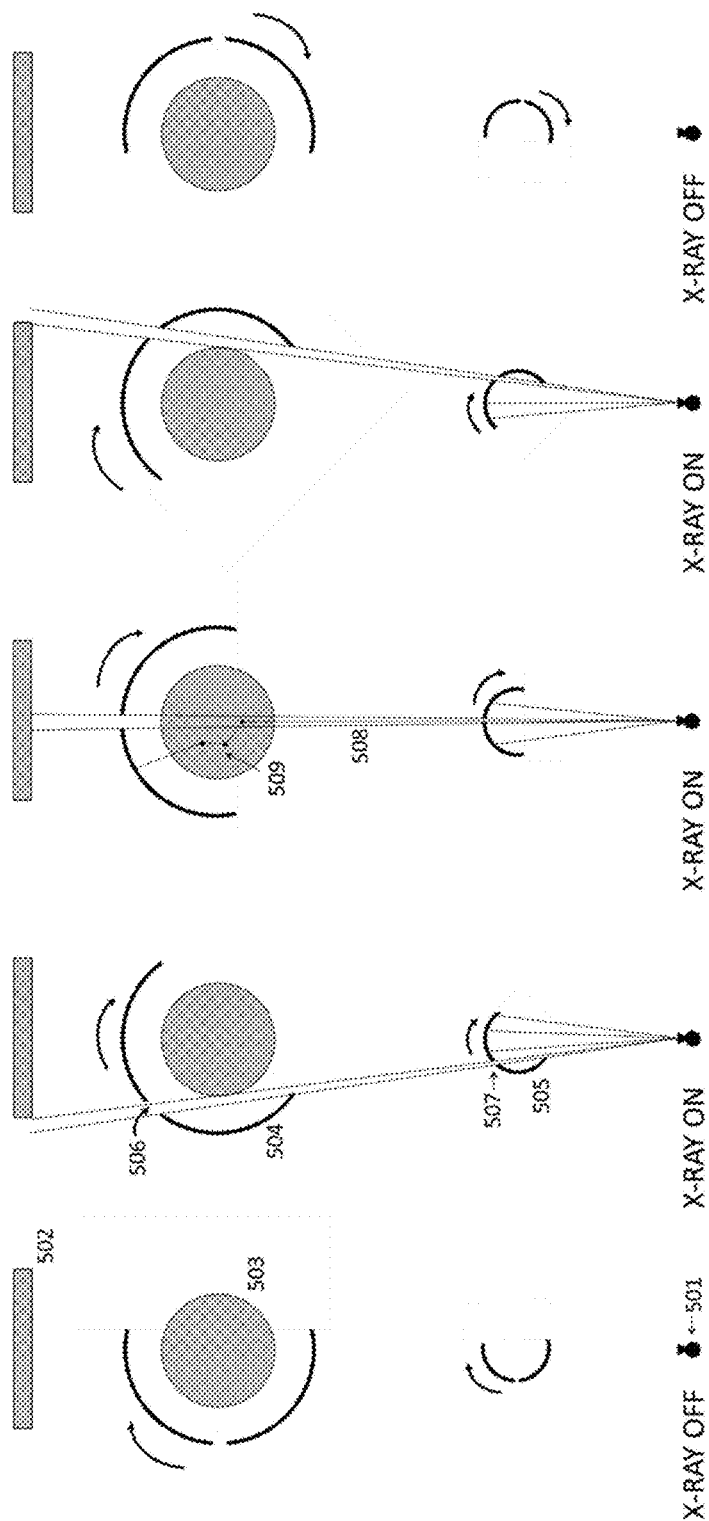
FIGS. 5A-5E provide a series of schematic views of the imaging system that show the method of imaging of a dedicated CT imaging system equipped with FG-SS apparatus.

In FIGS. 5A-5E, planar views of the scanner geometry depicted in FIG. 4 are illustrated. In this setup, an x-ray source 501 generates an x-ray beam towards the x-ray detector 502 with the anatomy of interest placed within the FOV 503. The SS drum 504 is set to rotate around the FOV at a constant speed. The FG drum 505 is positioned between the source and FOV and is set to rotate with the same rotational speed as that of the SS drum. Projection of x-rays onto the FOV does not commence, as shown in FIG. 5A, until the SS window and the FG window align with a line of sight from the source to the detector panel, as shown in FIG. 5B. During the entirety of the x-ray projection on FOV, the SS window 506 is positioned on the path of the x-rays, between the FOV 503 and the detector panel 502, while both the FG and SS drums continue to rotate synchronously with a constant speed. X-ray photons that enter the FG drum are either fully absorbed or back-scattered, excepting those aligned with the FG window 507. The photons within the generated narrow beam 508 enter the patient's anatomy. Depending on the composition of the body part and the quality of the beam, some of the photons are scattered. The scattered photons, such as 509 displayed in FIG. 5C, undergo at least one scatter event and are eventually back-scattered or absorbed by the SS sheets 504 or the object of interest placed inside the FOV 503. Only those transitioning photons that are on the path of the SS window 506 can escape the SS drum to ultimately reach the detector. The beam that reaches the detector panel is mostly composed of primary photons that have transitioned through the patient body without scatter interaction. The x-ray exposure continues until the line of sight between the source, FG window, SS window and the detector disappears, at which time the x-ray exposure stops. X-ray production is then halted until start of the next exposure. During this time, the captured projection is acquired from the detector panel and stored in a memory unit. The positioning of the setup at five consecutive instances of time are illustrated in FIGS. 5A-5E. Following this process, the entire anatomy positioned in FOV is imaged as the narrow beam spans the entire fan beam. The resulting projection almost exclusively contains information of the primary photons.

Theory of Operation

Figure 6:
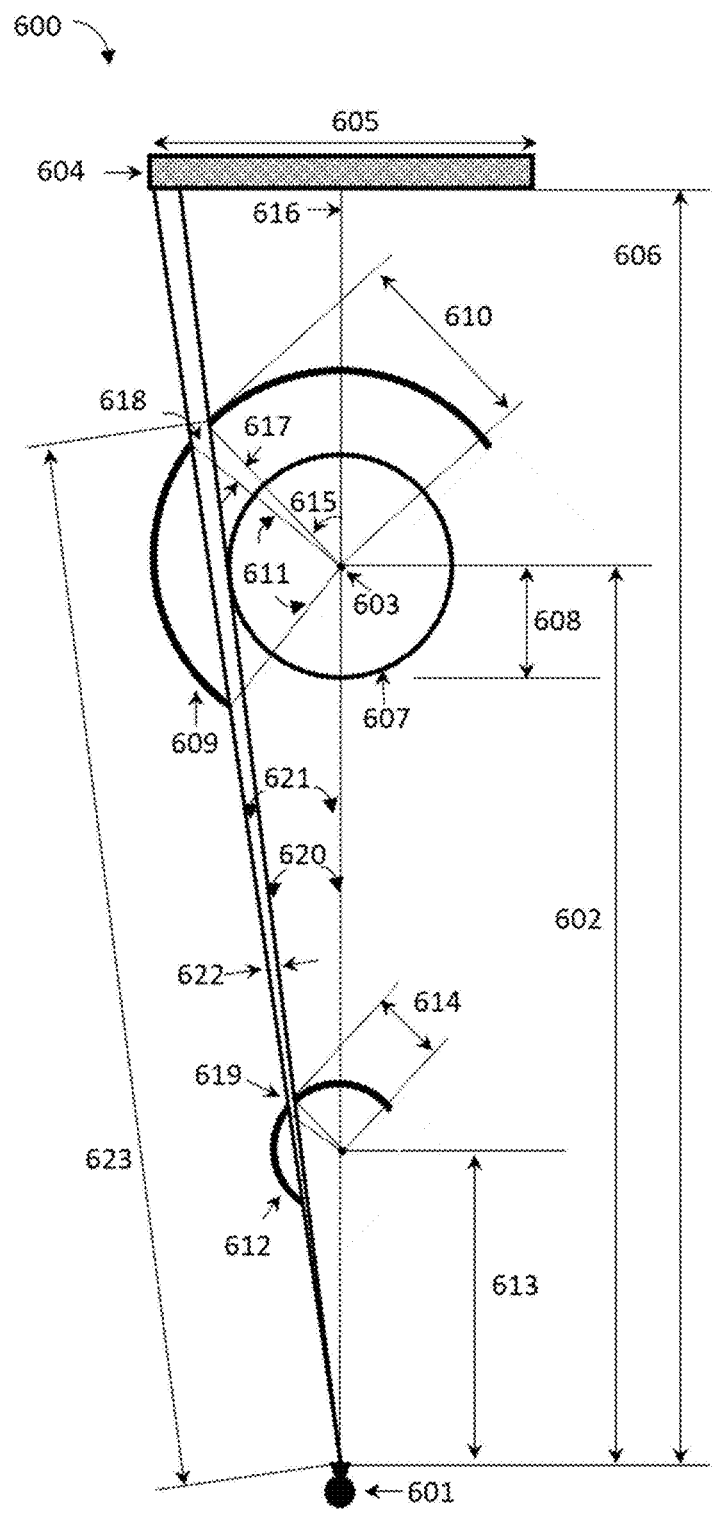
FIG. 6 is a schematic diagram of the imaging system outlining the geometry and theory of operation of the FG-SS apparatus.

FIG. 6 illustrates an exemplar schematic 600 of the geometry of a dedicated CT scanner equipped with FG and SS units. An x-ray source 601 is positioned at a distance 602 (herein referred to as the source-to-isocenter-distance (SIC)) from the center of rotation 603 (herein referred to as the isocenter) of the gantry of the CT system. A flat x-ray detector 604 with a width of D 605 is positioned at a distance 606 (herein referred to as the source-to-imager-distance (SID)) from the source. The cross section of the FOV of the imaging system is a circle 607 with a radius L 608. The rotational axis of the SS drum 609 is concentric with that of the FOV. The distance between the SS window 618 and the center of rotation of the SS drum is R 610.

In the diagram shown in FIG. 6, the sheets of the FG and SS drums have the same angular span. The maximum angular span of each wing of the SS or FG drums is symbolized herein as γ 611. The axis of rotation of the FG drum 612 is positioned with a distance C 613 from the source 601. The distance between the FG window and the center of rotation of the FG drum is r 614. During an image acquisition, the rotational speed of the FG and SS drums are equal. Both drums rotate circularly with the same angular velocity. Moreover, the created windows between the sheets of each drum rotate in the same phase such that the angular displacement α 615 of the SS window 618 from the central ray 616 is equal to that of the FG window 619. Similarly, the angular width β 617 of the SS window 618 is equal to that of the FG window 619. Because of the synchronized movement requirement of the both units, their relative size and positioning are interdependent and can be expressed as $$C = SIC \times \frac{r}{R}. \tag{1}$$

The angular width of the windows in both assemblies, β 617, is a design parameter and is dependent on the specific geometry of a CT system and requirements of the scan. An increase in the magnitude of this parameter's value results in a larger number of scattered photons to escape the SS drum and reach the detector, whereas a small value may require a longer time duration for acquiring a projection and consequently, a longer scan time. Therefore, an optimized value for β depends on the objective scan time and the tolerance level for the received scattered photons on detector.

For each projection and with the rotations of the FG and SS drums, there is a time instance where the windows become aligned with the line of sight between the source and detector. The starting fan angle θ 620 of the narrow beam at this time instance is calculated as $$\theta = \operatorname{atan}\left(\frac{R \times \sin(\alpha)}{SIC + R \times \cos(\alpha)}\right). \tag{2}$$

Similarly, the stopping fan angle η 621 of the narrow beam can be calculated as $$\eta = \operatorname{atan}\left(\frac{R \times \sin(\alpha + \beta)}{SIC + R \times \cos(\alpha + \beta)}\right). \tag{3}$$

Given the values of θ and η parameters, the projected fan angle width ϑ 622 of the narrow beam can be derived by subtracting the two fan angles, $$\vartheta = \eta - \theta \quad (4).$$

From the point of view of the source, the value of ϑ changes during a projection as FG and SS drums rotate. Depending on the angular displacement of the windows, the reticle width at the source is calculated as $$w = J \times \vartheta \quad (5),$$

where J 623 is the distance between the SS window 619 and the x-ray source 601 and can be calculated as $$J = \frac{R \times \sin(\alpha)}{\sin(\theta)}. \quad (6)$$

The magnitudes of the narrow beam fan angle (ϑ) and the SS window distance from the source (J) change during a projection acquisition. At the maximum θ value (corresponding to the starting point of a projection as displayed in FIG. 5B), ϑ and J are minimized. With the rotations of the drums, the magnitude of θ decreases while the magnitudes of ϑ and J progressively increase until reaching their maximum as the SS and FG windows become aligned with the normal ray as displayed in FIG. 5C. As the rotation of the assemblies continues, the magnitudes of ϑ and J decrease until the current projection's x-ray exposure is terminated as θ reaches its maximum magnitude, displayed in FIG. 5D. The overall outcome of these movements is a constant change in the magnitude of the reticle width, w, as defined in Equation 5. This outlines the fundamental fluence modulation technique in the disclosed invention.

In the fluence modulation technique described above, an infinitesimally small width for the FG sheets is assumed. In practice, the sheets are constructed of highly x-ray attenuating material, such as tungsten, with a limited thickness—from a fraction of a millimeter to a few millimeters—depending on the beam energy and the constituting materials.

Figure 7:
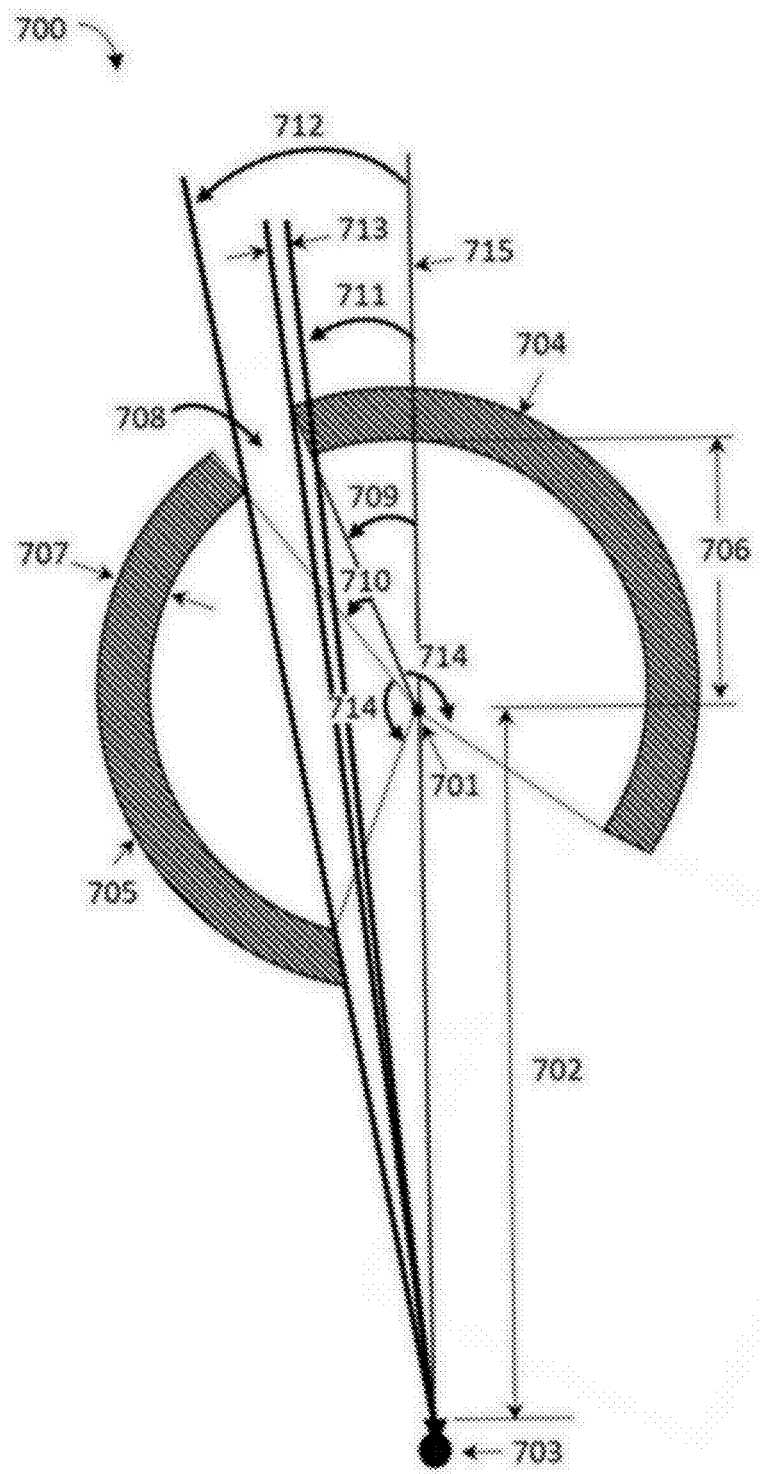
FIG. 7 is a schematic diagram of the FG unit outlining its geometry.

In FIG. 7, the changes in the reticle width of the narrow beam as a function of the thickness of the FG sheets are depicted. The same nomenclature used in describing the setup outlined in FIG. 6 is used for FIG. 7. In the FG setup 700, the center of rotation 701 of the FG drum is positioned at a distance C 702 from the x-ray source 703. The FG drum is made up of a semi-circular sheet 704 on one side of the FG window 708, and a semi-circular sheet 705 on the other side of the FG window 708. Both sheets are positioned concentrically; the point of the sheet centers is the same as the center of rotation 701 of the FG drum. The radius from the center of rotation 701 to the innermost boundary of each sheet is parameterized as r 706. The thickness of each sheet is parametrized as t 707. In the outlined setup, the FG window 708 is at an angular displacement α 709 from the imaging system's central ray 715. The angular size of the window is β 710. The modulated beam is generated at the source and is projected onto the imaging system's FOV through the FG window. If the thickness of the sheets is infinitesimally small, the angular span of the modulated beam starts from angle θ 711 and stops at angle η 712 from the central ray. In practice, the thickness t 707 is a nonzero value. This results in reducing the angular span of the modulated beam by a nonzero magnitude of δ 713, which can be calculated as $$\delta = \operatorname{atan}\left(\frac{(r+t) \times \sin(\alpha)}{C + (r+t) \times \cos(\alpha)}\right) - \theta. \quad (7)$$

This design leads to a modified narrow fan angle width ϑ (previously defined in Equation 4) calculated as $$\vartheta = \eta - \theta - \delta \quad (8).$$

Following Equations 7 and 8, changing the distance of the FG drum from the source (C), the size of the FG drum (r), and the thickness of the FG sheets (t) results in adjusting the narrow fan angle width (ϑ, defined and Equation 8) and consequently, the size of the reticle width (w, defined in Equation 5). Adjusting the window width results in modulating the number of photons that exit the FG drum. Therefore, the fluence modulation technique presented in this invention is achieved by continually changing the collimation of the total span of the sourced photons as the FG drum rotates, rather than applying filtering a portion of the beam.

In addition to finding a value for the narrow beam width, defining an optimal value for angular span of each sheet of the SS drum is an optimization problem that depends on two criteria. On one hand, an increase in this parameter leads to preventing more scattered x-rays from reaching the x-ray detector. This, however, may lead to blocking a portion or the entire narrow beam from entering the FOV. The angular span of each sheet of the FG drum, parameterized here as γ 714, must be set to prevent collimating the beam that will be transitioning through the FG window 708 before entering the FG drum. The maximum value of this parameter, as is displayed in FIG. 7, can be calculated as $$\gamma = \pi - 2 \times \operatorname{asin}\left(\frac{C \times \sin(\eta)}{r}\right). \quad (9)$$

Comparison to an Ideal Modulator

Ideally, fluence modulation will correspond to variations in the x-ray attenuation profile of the anatomy. In other words, as the level of attenuation changes, the fluence introduced to the anatomy should change accordingly. The case of perfect fluence modulation in correspondence to x-ray attenuation is referred to herein as an Ideal Modulator.

The fan beam attenuation profile of the FOV circle entirely filled with a material with linear attenuation coefficient of μ is defined as $$P(\theta) = 2\mu \sqrt{L^2 - (SIC \times \sin(\theta))^2} \quad (10),$$

where L is the radius of the FOV and θ is the fan angle between a photon and the normal ray of the imaging system. Employing the assumption that the only attenuating material between the source and detector is within the FOV, the number of photons (N(θ)) received at the detector element located at the fan angle θ follows the Beer-Lambert law, $$N(\theta) = N_0(\theta) e^{-P(\theta)} \times M(\theta) \quad (11),$$

where $N_0(\theta)$ is the unattenuated number of photons received by the same detector element. The auxiliary parameter M(θ) is a real value between zero and one describing the modulation properties of the FG drum. The most attenuated beam is the beam traversing through the thickest part of the FOV which corresponds to fan angle zero (θ=0, defined in Equation 2). The modulation parameter for this beam is set to one (M(0)=1), implying that no modulation occurs that may lead to terminating a portion of the photons within the beam. At nonzero fan angles however, this parameter is set to a value less than one, denoting that a proportional fraction of the photons within the beam are terminated before entering the FOV. The primary goal of a beam modulator is to equalize the number of photons received at detector element ($N(\theta)=N(0)$). Therefore, $$M(\theta)e^{-P(\theta)} = e^{-P(0)} \qquad (12)$$

or, $$M(\theta) = e^{2\mu\left(\sqrt{L^2-(SIC \times \sin(\theta))^2} - L\right)}.$$

Equation 12 describes an Ideal Modulator as a function of fan angle.

Figure 8:
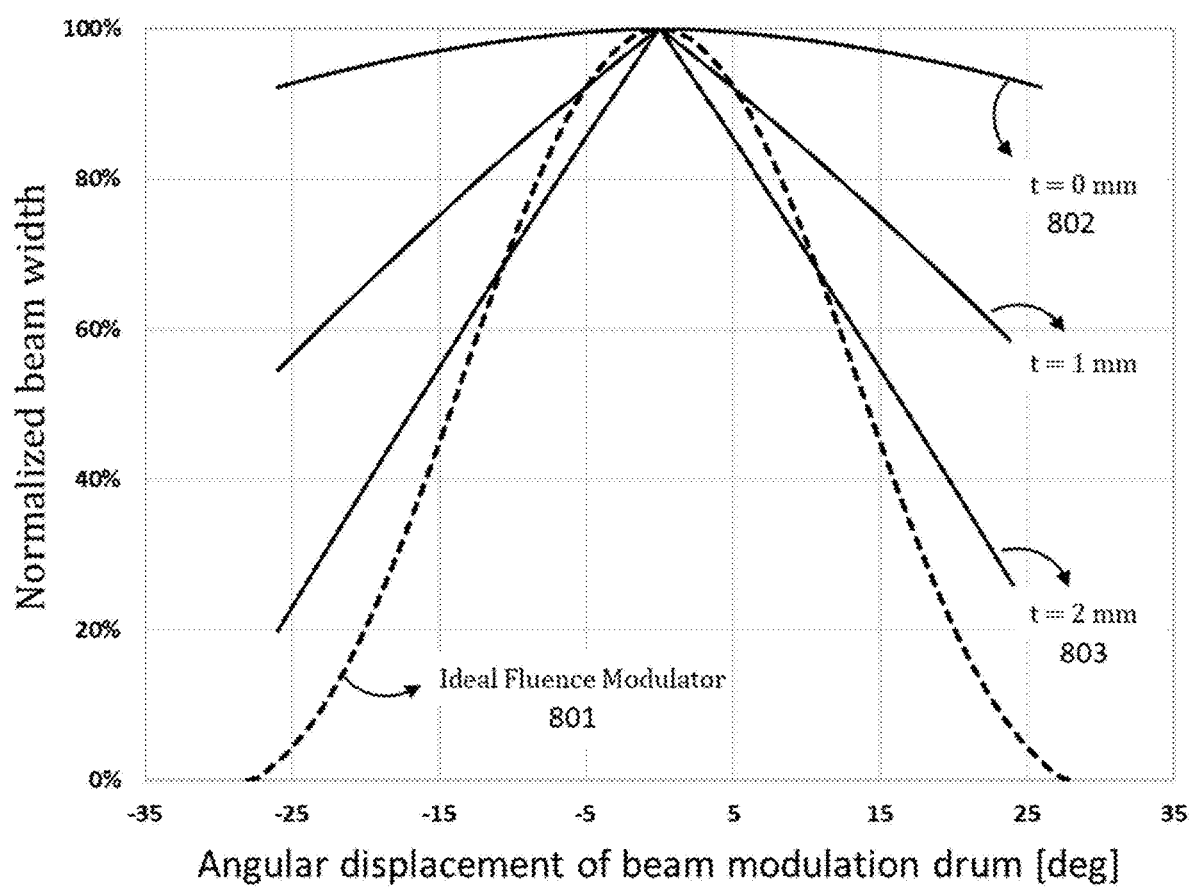
FIG. 8 provides a comparison between the resulting modulated beams from an ideal fluence modulator and that of the FG unit.

FIG. 8 illustrates the results of modifying the thickness of the FG sheets. These exemplar measurements were made using a CT system with SIC of 50 centimeters (cm), SID of 70 cm, R of 20 cm, r of 5 cm and β of 10 degrees. The dashed line 801 provides a reference for comparing the results to that of an Ideal Modulator design, as derived by Equation 12. The various curves illustrate the change in the perceived narrow beam (w, derived in Equation 5) as a function of the angular displacement of the FG window from the normal ray (a) and the thickness of the beam shaping sheets (t). Here, the assumption is that the sheet is made up of a highly attenuating material that absorbs x-rays upon an interaction. As shown in the result 802, in the theoretical case of an infinitesimally thin sheet (t=0), the drop in w as the FG window moves from the zero angular displacement (α=0) to the maximum angular displacement (α=25.94 degrees) is less than 10%. As the thickness of the FG sheet is increased, however, this drop also increases. For instance, in the case of a t=2 mm 803, less than 5% of the incident beam on the FG window can exit the window at maximum angular displacement of the FG window. By comparing the case of t=2 mm beam width to the Ideal Modulator 801, it is critical that the FG beam modulator replicates the performance of an Ideal Modulator regarding its tolerance of some degree of error. The comparative maximum error levels are observed at the angular displacement close to zero (where the beam modulator window collimates too much of an incident beam) and close to the maximum displacement angle (where the beam modulator collimates too little of the incident beam).

Alternative FG-SS Embodiments

Figure 9:
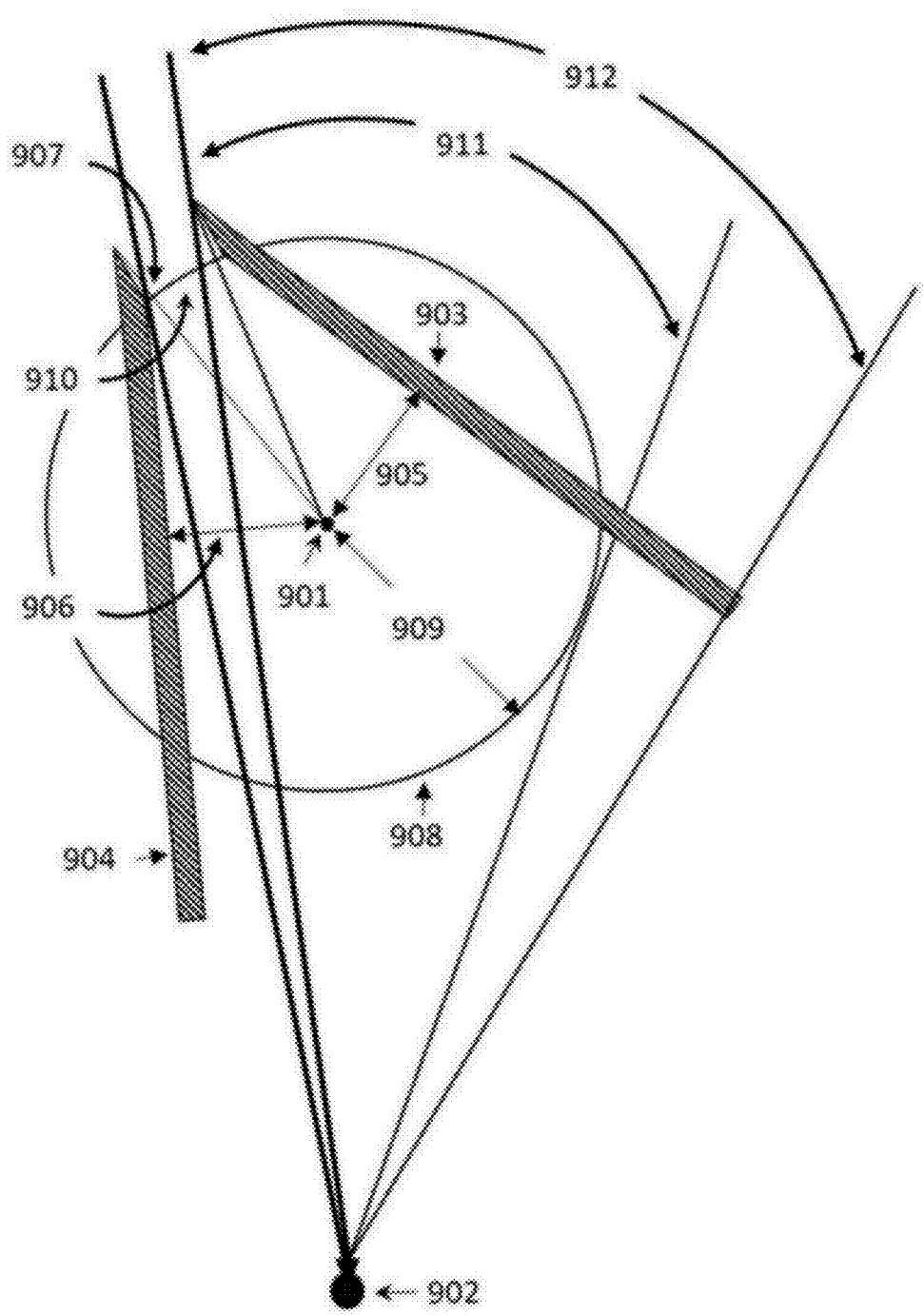
FIG. 9 is a schematic diagram of the FG unit incorporating flat sheets.

Defining circular shapes for the sheets is not a necessary requirement for the performance of the disclosed modulation technique. The sheets can be designed as flat plates, installed within the FG or SS units. FIG. 9 illustrates an embodiment of the invention where a setup is described for utilizing flat sheets in the FG drum. The center 901 of the FG drum is positioned at a distance from an x-ray source 902. The drum is composed of a flat sheet 903 and another flat sheet 904. In the setup displayed in FIG. 9, both sheets are positioned at the same distance from the center of rotation such that the perpendicular distance 905 of a sheet 903 from the center of rotation 901 of the drum is equal to the perpendicular distance 906 of the other sheet 904 from the center of rotation 901 of the drum. For each sheet, one tip 907 is placed on the circumference of a circle 908 with a radius 909, positioned concentrically with the rotation axis of the drum. Following this, a gap 910 is formed between the sheets which is the FG window.

A benefit of the FIG. 9 layout is its extended collimating capability. Using the circular sheet design, the collimation angle 911 is defined as the angular coverage of a circular sheet preventing the FOV and the detector from x-ray photons that are not traversing through the FG window. Using a planar sheet 903 however, the collimation angular coverage 912 can be increased. The extent of the increase depends on the length of the planar sheet 903.

A similar design can be used for the SS unit. In this case, the SS unit is formed of two flat sheets placed at an angle with respect to each other such that a gap, akin to that of the FG unit, is created between the sheets. As a result, scattered rays are blocked; only primary photons transitioning through the SS window reach the sensitive area of the x-ray detector.

In FIGS. 10A-10E, planar views of the scanner geometry employing the FG and SS units at five instances of time during a single projection acquisition are illustrated. The FG unit 1001 and the SS unit 1002 are placed between an x-ray source 1003 and an x-ray detector 1004. The SS drum rotates around the FOV 1005 such that the lateral edges of its sheets sweep around an imaginary circular path 1006. Similarly, the FG drum rotates such that the ends of its sheets sweep around an imaginary circular path 1007.

Figure 10E:
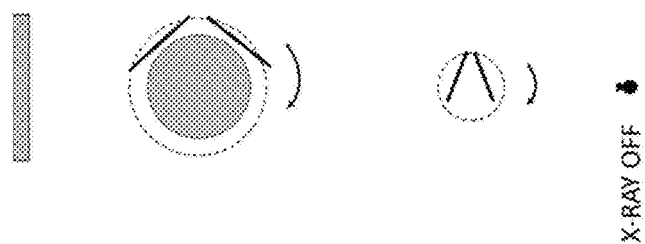
FIGS. 10A-10E provide a series of schematic views of the imaging system that show the method of imaging of a dedicated CT imaging system equipped with the flat sheet FG-SS apparatus.
Figure 10D:
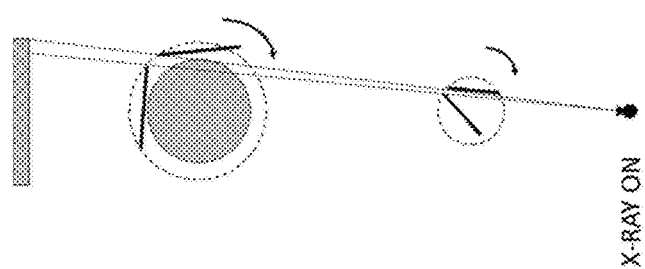
Figure 10C:
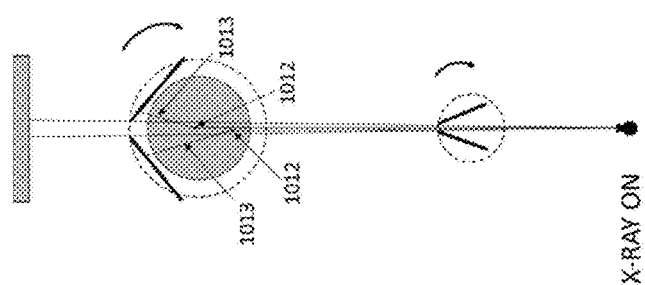
Figure 10B:
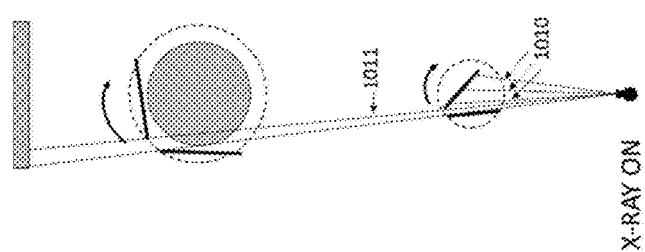
Figure 10A:
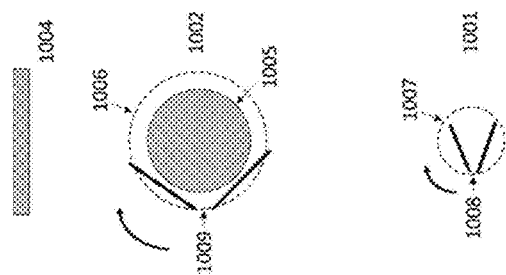

During the continuous rotations of the FG and SS drums, the x-ray source is in OFF state (x-rays are not generated) by default. Two examples of the scanner geometry setup are shown in FIGS. 10A and 10E. As soon as the x-ray source, FG window, SS window and the x-ray detector are aligned along a line—such that a photon generated at the source can travel through the FG window 1008 and the SS window 1009 without an absorption or scatter interaction with the FG or SS sheets—the source transitions to the ON stage (x-rays are generated). This time instance is depicted in FIG. 10B.

Generated photons 1010 that are not traveling toward the FG window are absorbed by the FG sheets. During the rotations of the FG and SS drums, the anatomy of interest, placed in the FOV, is exposed to radiation by the x-ray photons within the beam 1011 that is formed by the FG unit. Some of the photons within this beam undergo coherent or incoherent scatter events 1012. Depending on the composition of the object in the FOV and the interacting photon energy, these photons are scattered away 1013 from their primary paths and are absorbed by the scatter sheets. After exposing the entire FOV, as displayed in FIG. 10D, the source transitions to the X-RAY OFF state and the exposure stops. This state is displayed in FIG. 10E. The rotations of the drums continue until the start of the next projection, and the same sequence of events is repeated.

Mechanics to Accomplish Anatomical Specificity

In designing the FG-SS apparatus for dedicated CT systems, accounting for and adjusting according to the size of the object of interest is critical. The same organs vary in size from patient to patient. For example, in the case of a dedicated extremities CT system, the radius of the arms or legs of different patients is expected to vary significantly. An approach then, is to design a scanner geometry that fits the largest extremity size. This approach assumed a FOV diameter that is large. If a small extremity is put into the FOV, the resulting FG would then not match its actual size. As a result, the dose introduced to the extremity would be higher than in the case of a design optimized for a smaller extremity. On the other hand, if the system is designed to match the requirements for imaging an average extremity and the extremity in FOV is large, the photon count received from the area of the extremity far from its center may be insufficient to render a high quality acquired image. In addition, the shape of the cross-section of the body part in the FOV may be elliptical—this would be in contradiction to the circular cross-section assumption of the FOV of a dedicated CT system. Lastly, the diameter of the FOV may change in different slices. For example, this would be the case for both breast CT and head CT, where a cylindrical shape with constant cross-section size does not fully approximate either organ of interest.

Figure 11:
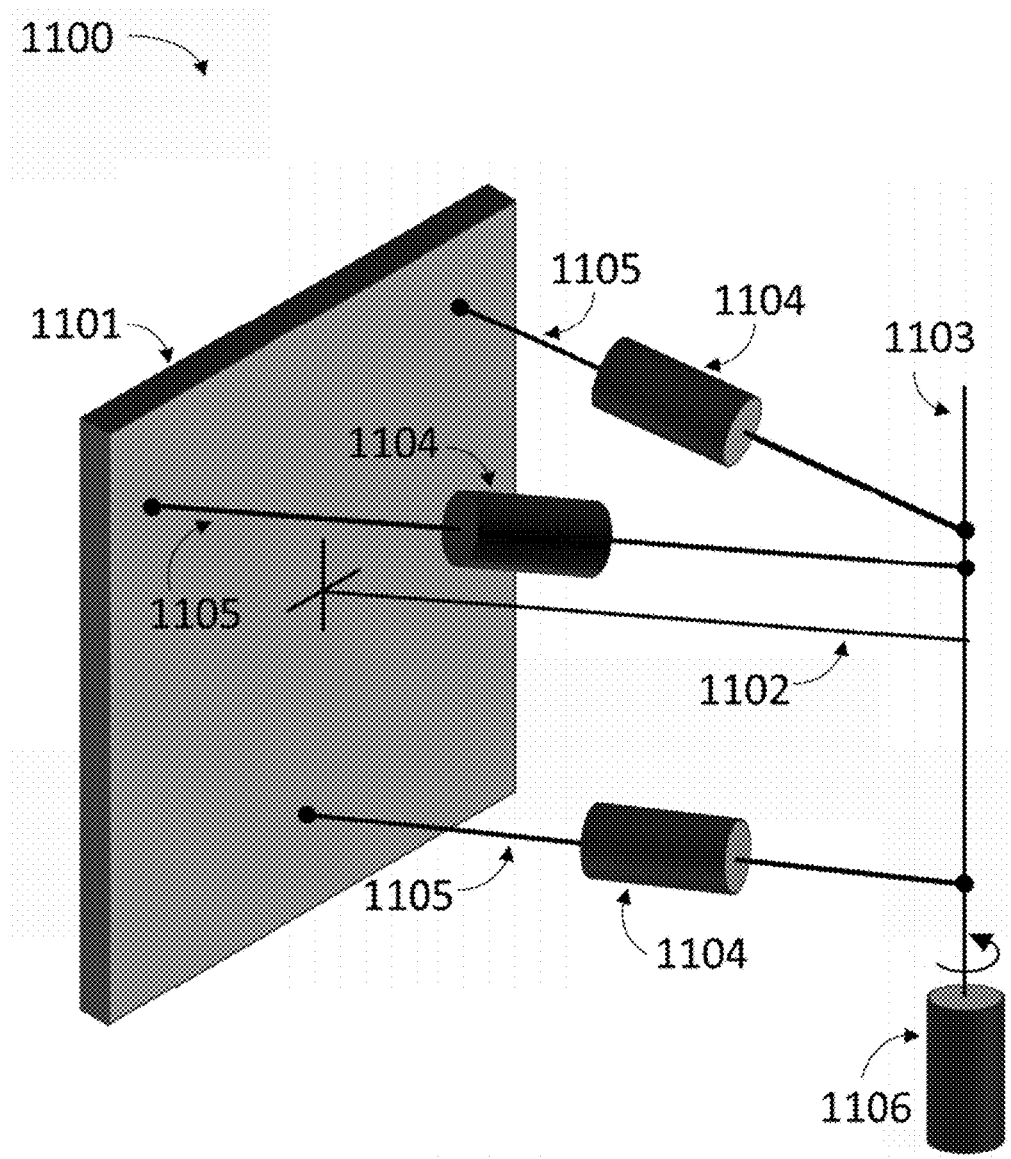
FIG. 11 shows the design of the robotics of every sheet of the FG and SS unit.

By adjusting the radius of the SS drum and tilting of SS sheets, and accordingly, the radius, tilting and distance between the center of rotation of the FG assembly and the x-ray source, one can account for the specific requirements of an anatomy. FIG. 11 illustrates an embodiment of the invention designed to provide four degrees of freedom adjustment for the sheets of the FG drum. The SS drum can adopt the same model 1100. The sheet 1101 is positioned within a specific distant 1102 from the axis of rotation 1103 of the drum. The sheet is attached to three actuators 1104 through three separate prismatic joints 1105. By adjusting the length of the joints, the tilting and the distance of the sheet from the axis of rotation can be adjusted. The size of the window between two sheets can be adjusted by providing an actuator 1106 that rotates the sheet and the prismatic joints and the associated actuator around the center or rotation of the drum.

Figure 12:
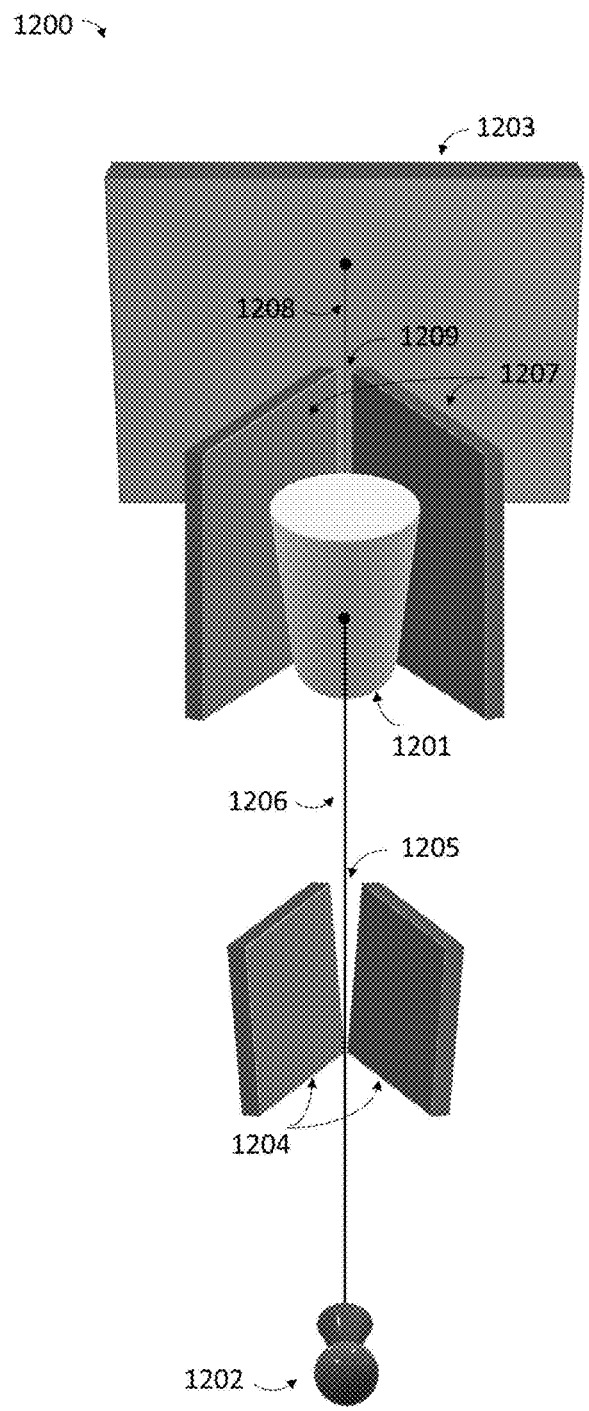
FIG. 12 is a perspective view of the imaging system with variational fluence modulation along the cone angle.

The design and method of operation outlined in FIGS. 10 and 11 enables flexibility in modulating the beam depending upon the shape and composition of the anatomy placed in FOV, the expected dose distribution, and the dynamic range of the x-ray detector. FIG. 12 provides an exemplar illustration 1200 where an object 1201 is placed between an x-ray source 1202 and an x-ray detector 1203. The tilting of the FG sheets 1204 leads to forming the FG window 1205 that is wider on the top than the bottom. As a result, the beam 1206 that is projected onto the object within the FOV is wider on the top of the object than its bottom.

One utilization of this setup is for scanning pendent breasts. The breast diameter is larger at the posterior parts of its anatomy, the region close to the patient's chest wall, than its anterior. Exposing a breast to a uniformly shaped beam results in large non-uniformities in the absorbed dose in breast. The scattered photons in the object are absorbed into the SS sheets 1207. Only the primary photons 1208 that are aligned with the SS window 1209 can pass through the SS window and reach the detector panel.

Data Flow

Figure 13:
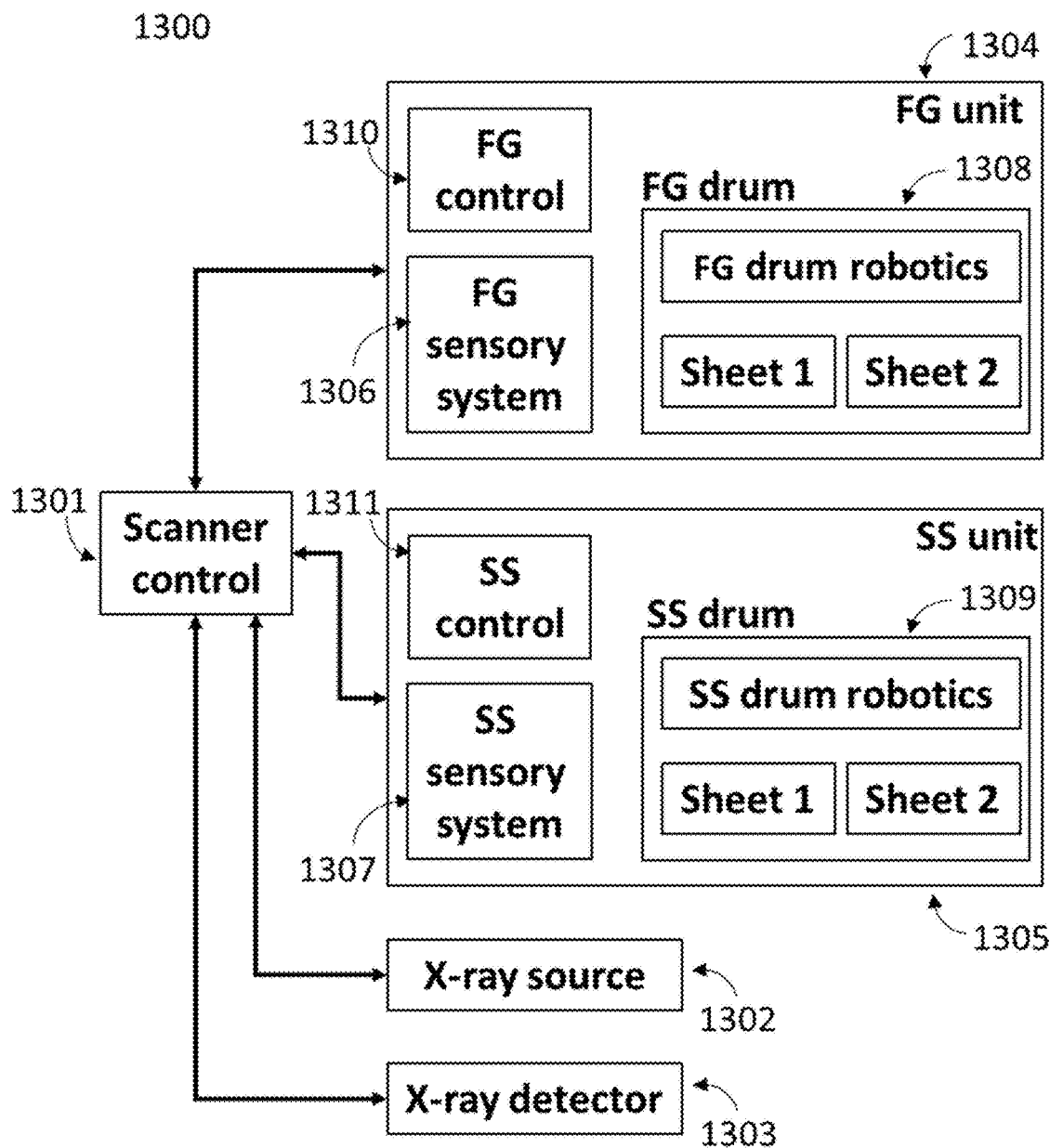
FIG. 13 illustrates the main units of a CT imaging system equipped with the FG-SS apparatus and the data flow between the imaging system components, an exemplar computer system, x-ray source and detection units, in accordance with embodiments of the present subject matter.

The processes involved in the flow of data between different parts of a CT system for an FG-SS enabled image acquisition are illustrated in FIG. 13. As outlined 1300, the five main components involved in the image acquisition are the scanner control unit 1301, the x-ray source 1302, the x-ray detector 1303, the FG unit 1304 and the SS unit 1305. Timing of image acquisition and synchronization between different units is controlled via the scanner control unit 1301. X-ray source unit 1302 embodies the x-ray generator, the x-ray tube and the associated electronic interface that results in the generation of an x-ray exposure. The x-ray detector unit 1303 embodies the detector panel, the image storage and the electronic interface for transferring the acquired images. In one embodiment of the invention, two sensory units 1306, 1307 are used to define the timings of the x-ray exposure and detector frame readout and to synchronize the motions of the FG drum 1308 and SS drum 1309, accordingly. Each sensory unit is composed of at least one sensor which is installed on the gantry or the corresponding unit with a fixed position with respect to the gantry. The communication and exchange of data between the scanner controller 1301 and the FG and SM units are possible through the FG control system 1310 and SS control system 1311, respectively.

Timing of X-Ray Exposure

The operation outlined in FIGS. 5B, 5C and 5D describe an x-ray exposure period during which the x-rays are produced. As rotations of the FG and SS units occur, the generation of x-rays at the source results in partial shielding of the patient body and x-ray detector from the generated photons. Therefore, x-ray production at the source must occur only when the SS unit window is positioned between the patient and the detector—when the reticle from the source to the detector provides a clear line of sight. A similar case exists for the FG drum in that the x-ray must be projected only when the FG window is on the side of FOV rather than being on the side of the source.

Figure 14:
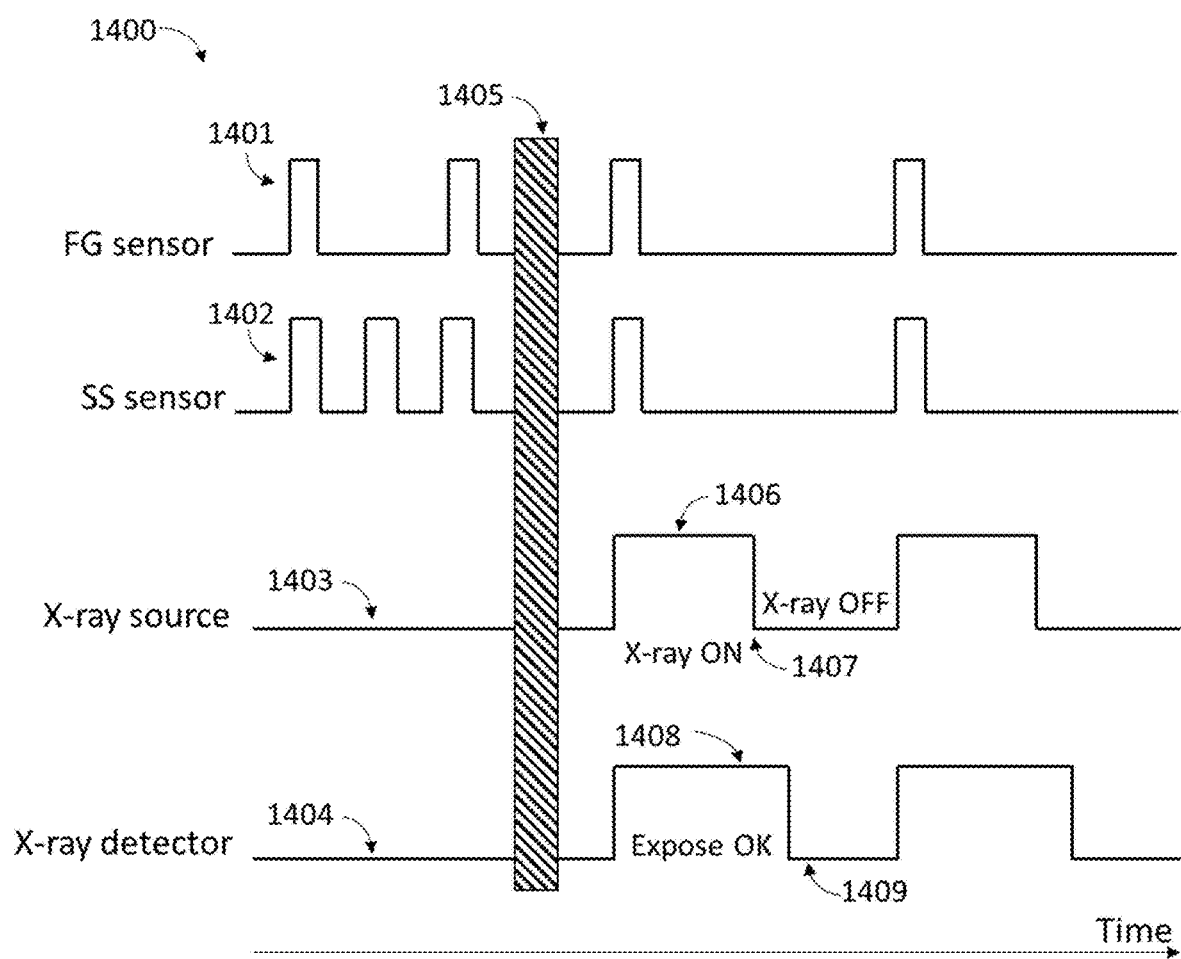
FIG. 14 is a diagram illustrating the synchronization of the robotic motions of the FG and SS assemblies with the x-ray generation and detection units.

FIG. 14 illustrates an exemplar method in accordance with the embodiments described herein. In this method 1400, at start of the rotational movement of the FG and SS drums, the signal 1401 received from the FG sensor is not synchronized in time with the signal 1402 received from the SS sensor, x-rays 1403 are not produced and the projections 1404 are not recorded. With the progression of time and during an adjustment time period 1405, the rotational speed of the FG and SS drums are adjusted through the control units of the scanner, FG and SS units. At the end of the adjustment period, the FG and SS drums have reached their nominal speeds and are synchronized in motion such that the feedbacks from the corresponding sensory systems are similar. The x-ray source generates x-rays during the time period 1406 in which the FG and SS windows are aligned with the source and the detector panel. Upon alignment becoming invalid 1407, the x-ray exposure stops. The timing of the detector is controlled such that the exposure occurs only during the period to time that the panel is ready to receive the x-ray photons. This period, referred to as the Expose OK 1408, is followed by a time period 1409 for collecting the capture frame and transfer to a storage system. This sequence of events continues until the completion of the scan procedure.

Scanning Procedure

Figure 15:
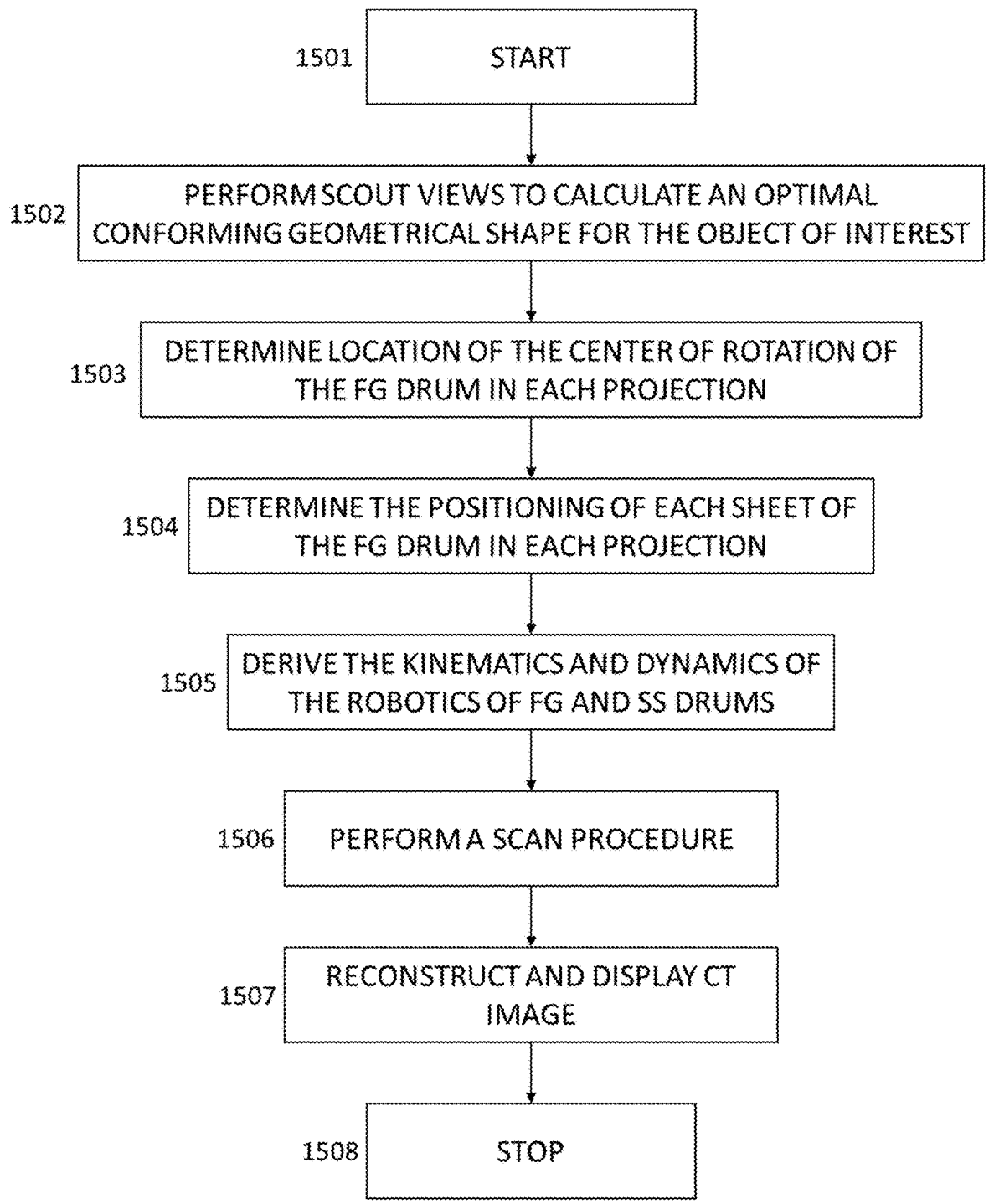
FIG. 15 is a high-level flow chart of a typical scan procedure using a CT system equipped with the FG-SS apparatus.

A stepwise flow chart, outlining the major processes involved in performing a scan on a CT system equipped with the disclosed FG-SS apparatus, is shown in FIG. 15. At start 1501, the patient is positioned in the scanner such that the body part of interest is placed in the imaging system's FOV. In the next step 1502, a set of pre-scan scout view projections are captured to find the optimal shape of the object in scanner's FOV. The optimal shape can have a circular or elliptical cross section, cylindrical or ellipsoidal axially and misaligned from the isocenter of the imaging system. Given the estimated shape of the object, the positioning of the sheets and the center of rotation of the FG drum in each projection are calculated in the following two steps 1503-1504. The robotics of the FG drum assembly must be able to support the motions of the sheets and the drum during a scan procedure. Therefore, a specific set of values are defined in the next step 1505 for the robotics of the FG and SS drums. A scan is performed in the following step 1506, images are transferred to processor for image reconstruction and display 1507. This marks the final step in performing a scan while modulating the fluence and rejecting the scattered photons.

Results

An exemplar cone beam CT system with SIC of 50 centimeters (cm), SID of 70 cm, R of 20 cm, equipped with an FG-SS apparatus with r of 5 cm and (f of 10 degrees, was used for the simulations presented herein after.

Detected Fluence

Figure 16A:
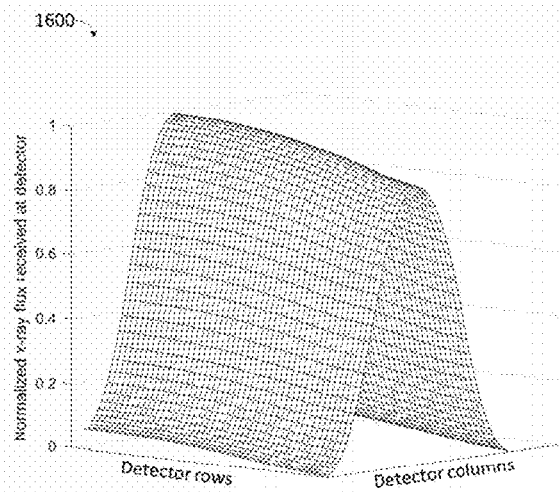
FIGS. 16A-16D provide examples of beam modulated x-ray fluence received at a dedicated CT system x-ray detector.
Figure 16B:
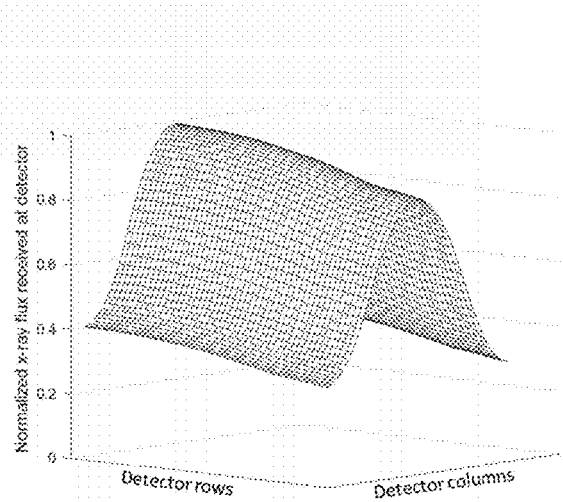
Figure 16C:
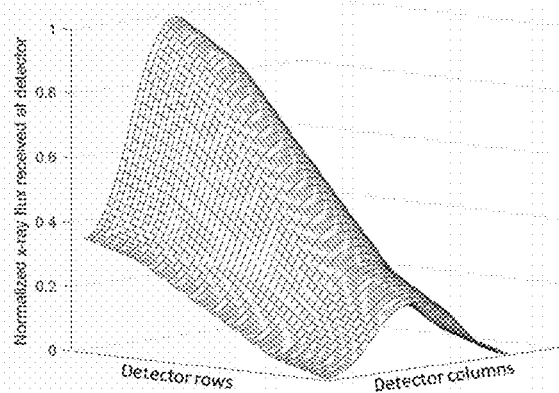
Figure 16D:
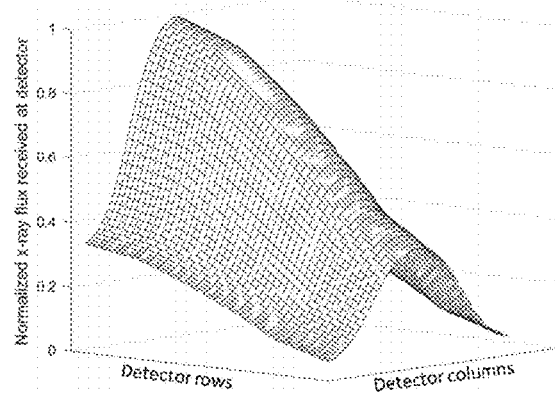

FIGS. 16A-16D illustrate examples 1600 of the modulated fluence in absence of a body part to highlight the capabilities of the FG unit in modulating the x-ray fluence projected onto the FOV. The setup is such that the scanner system's normal ray is incident on the detector panel on the top row and middle column. If the positioning of the sheets of the FG drum are adjusted to image a cylindrically shaped anatomy, such as the extremities, the received fluence upon the detector would be similar to the profiles shown in FIGS. 16A and 16B. The diameter of the cylinder in the case of FIG. 16A is assumed to be smaller than the case in FIG. 16B, therefore, the distribution of the fluence is sharper in the middle columns of FIG. 16A than in FIG. 16B. If the object of interest has an ellipsoidal shape, the fluence distribution changes in both fan and cone directions. Adjusting the beam size is accomplished by tilting the surface of the sheets as described in FIG. 11. An example of an ellipsoidal body part is a pendent breast. In the case shown in FIG. 16C, the small breast size was modelled. One will appreciate the fast fall off of the detected fluence in this case by moving away from the middle column of the detector. The result of modelling a larger breast is shown in FIG. 16D. The difference in the detected fluence in fan direction is accomplished by adjusting the window size.

FIGS. 17A and 17B illustrate the results 1700 of a computer simulation comparing dynamic range requirements in the detector of a CT system with and without an FG unit. Implementation of the FG unit results in a reduction in the required dynamic range. In this instance, a cylindrical body part, representing anatomy such as an extremity, was simulated.

Displayed in FIG. 17A is a projection 1701 acquired without FG; FIG. 17B is a projection acquired with FG. Area 1703, visibly light in color, illustrates regions of detector subject to an overexposure. The area 1702 of the acquired projection that corresponds to the line integrals through the cylindrical object is notably darker than the area 1703 that corresponds to no attenuation inside of the cylinder. In this setup, due to the large range from light to dark regions, the dynamic range of the detector must be broad to account for both highly attenuated, and unattenuated x-ray beams received at each detector element. Detector technology has a limited dynamic range in general. That limited dynamic range may result in saturation in the detector elements that receive a high level of x-ray fluence. In the case of low quantum statistics in highly attenuated x-ray beam that arrive at detector, the detected signal may not be differentiable from the quantum noise, resulting in low signal-to-noise ratio in the projections and reduced quality of the reconstructed images.

The results shown in FIG. 17B provide a visual representation 1704 of a key benefit to implementing FG. The pixels 1705 that correspond to the unattenuated beam are dark, implying that the x-ray fluence is modulated such that only the object within the FOV, in this case a cylinder, is exposed to x-rays. Therefore, only the pixels 1706 that receive beams that enter the cylinder are nonzero and carry the attenuation signal.

Line profiles in the displayed projections in FIGS. 17A and 17B across the horizontal line 1707 are compared in FIG. 17C. The profile 1708 associated with the non-FG case experiences a large non uniformity across the detector columns. The highest levels of signal are detected where unattenuated signals are received; the lowest levels of signal are detected at the pixels that receive the beam that have the longest line path. The profile 1709 displays more uniform characteristics, implying a significant decrease in the required detector's dynamic range. In the case shown in FIG. 17C, the dynamic range, defined here as the ratio of the maximum and minimum values of the parts of the line profiles that carry the breast projection signal, was reduced 89% from 240 (Arbitrary Unit [A.U.]) to less than 25 A.U. In addition to the reduction in the required detector dynamic range, the detected signals from the darkest pixels, the ones associated with the middle detector columns, are increased.

The results 1800 of modelling a breast in an FG-enabled cone beam CT system are illustrated in FIGS. 18A-18D. In the simulations, a homogenous semi-ellipsoid was used as a surrogate for a pendent breast. In this case, the fluence is modulated across both fan and cone angles. Visual comparison between the projections 1801-1802 acquired without (FIG. 18A) and with (FIG. 18B) FG demonstrates the improvements in uniformity of the acquired image which implies a significant gain in reducing the required dynamic range to acquire projections.

FIGS. 18C and 18D provide a quantitative comparison between the projections 1801-1802 acquired without and with FG. In the displayed results, the horizontal and vertical line profiles in each projection are associated with the positions of the horizontal 1803 and vertical 1804 lines shown in FIGS. 18A and 18B. In both cases, the uniformities of the profiles are improved with the implementation of FG. This implies that with the implementation of FG, the requirements for the dynamic range of the detector are more relaxed than the case without FG.

Scatter Detection

Figures 19A, 19B:
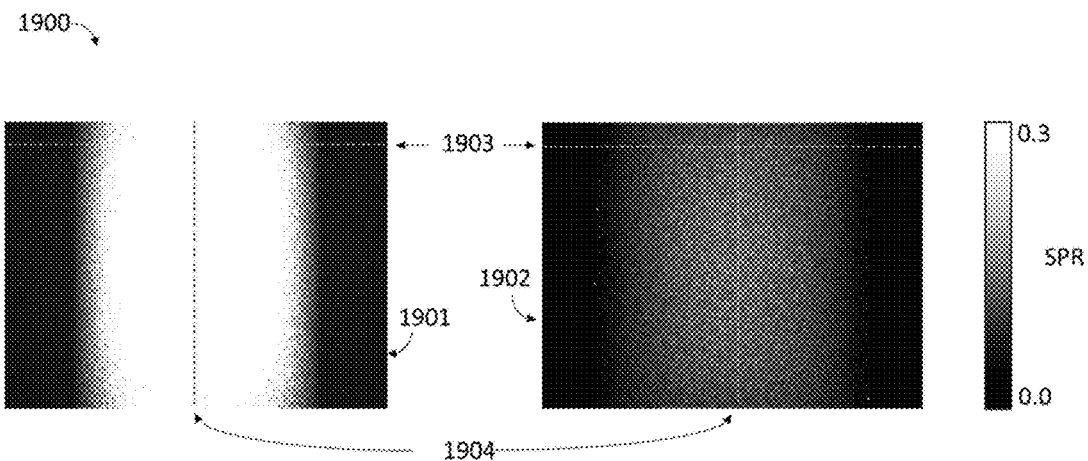
FIGS. 19A-19D illustrate simulation estimations of the SPR without and with usage of the FG-SS apparatus during imaging of a cylindrical phantom in accordance with embodiments of the invention, in addition to a comparison of a first line profile (without FG-SS apparatus usage) and a second line profile (with FG-SS apparatus usage) through the simulated projection images along the horizontal and vertical dimensions.

The combined usage of the FG and SS units can greatly reduce the acquisition of the scattered photons. In the case of a uniform cylinder, the results 1900 are displayed in FIGS. 19A-19D. The SPR image 1901 derived from a cone beam CT system without the FG-SS apparatus in shown in FIG. 19A. The SPR image 1902 derived from the same system, with the addition of the FG-SS apparatus, is shown in FIG. 19B. The same window levelling settings were used in both FIGS. 19A and 19B. One can appreciate that with the combined utilization of the FG and SS, the measured SPR can be significantly reduced throughout the projection of the cylinder.

Figure 19C:
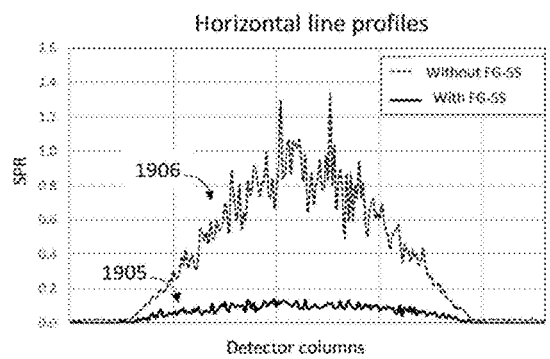
Figure 19D:
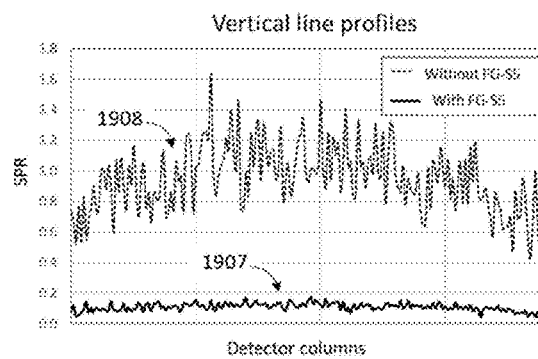

The line profiles of these SPR images across the horizontal 1903 and vertical 1904 lines are illustrated in FIGS. 19C and 19D, respectively. As the results show, the SPR across horizontal lines in reduced by almost an order of magnitude when comparing the resultant profiles when FG-SS is implemented 1905 versus not 1906. The SPR across the vertical remains relatively uniform. SPR with FG-SS implementation 1907 is nearly an order of magnitude smaller than when FG-SS is not implemented 1908.

Adjusting for Anatomical and Misalignment Factors

Figure 20:
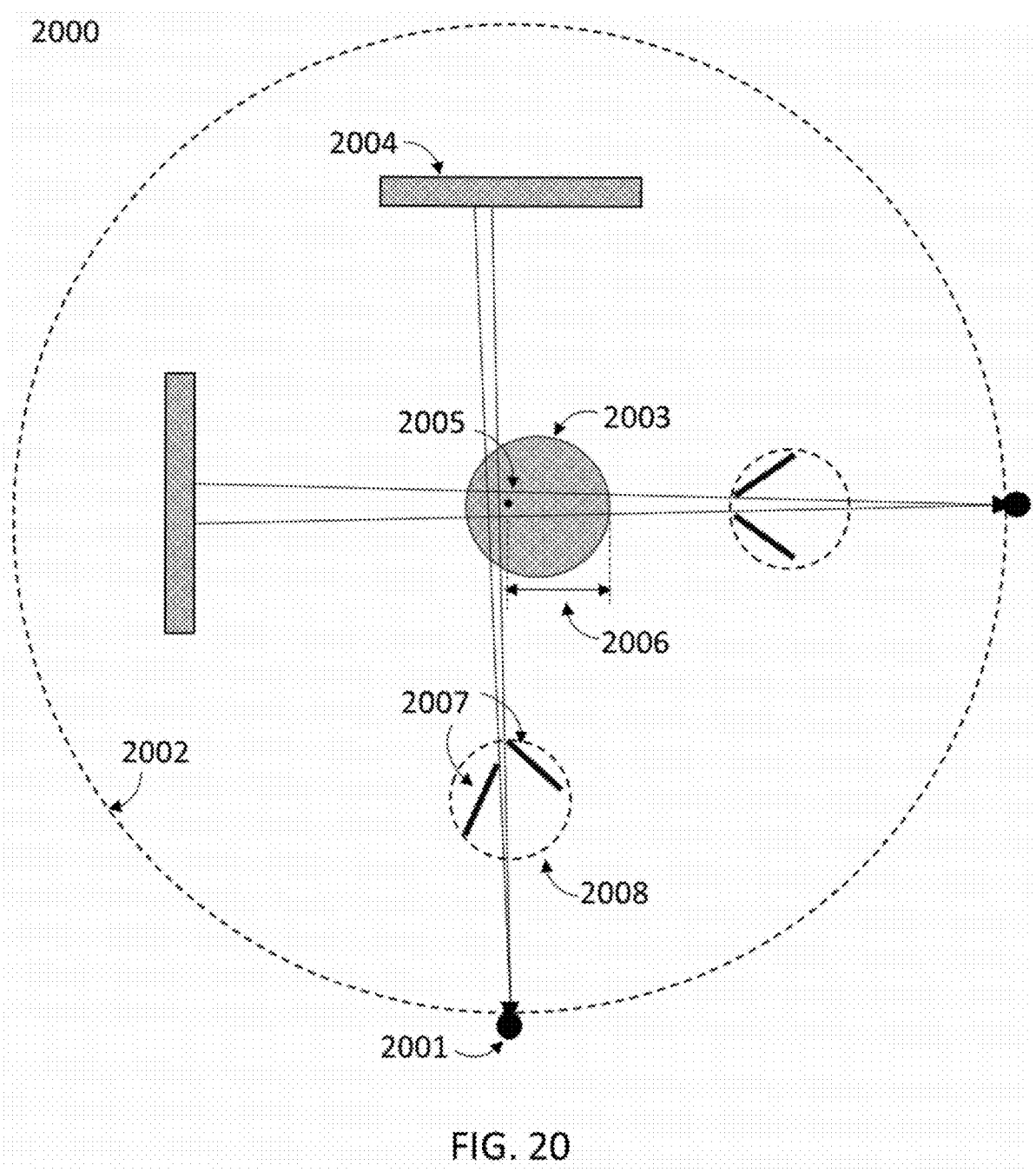
FIG. 20 illustrates the method of imaging an object positioned non-concentric with the isocenter of the CT imaging system equipped with the FG-SS apparatus.
Figure 21A:
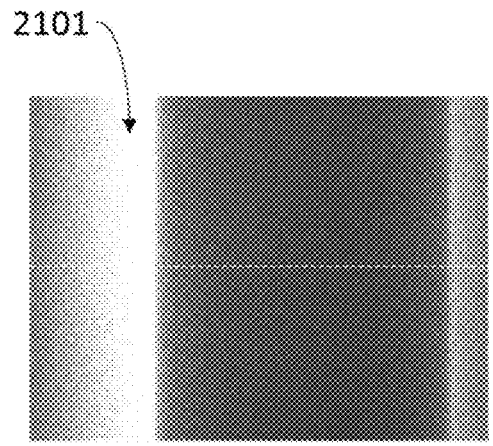
FIGS. 21A-21C illustrate an exemplar comparison between the cylindrical phantom scans with and without a correction for non-concentric alignment of the object and the isocenter.
Figure 21B:
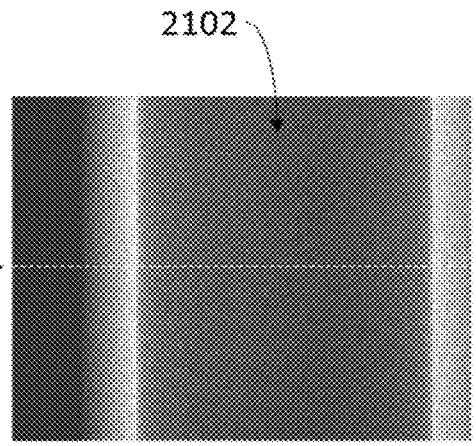
Figure 21C:
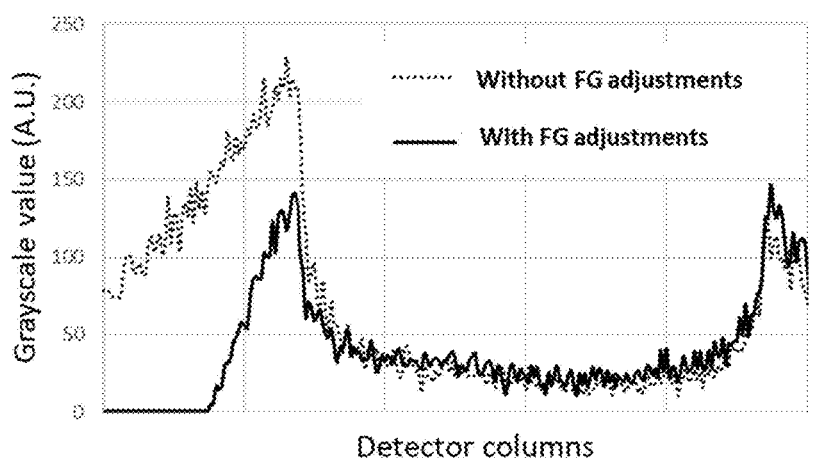

When imaging the anatomy, imperfect positioning with respect to the isocenter may arise. It may also be the case that anatomy has a circular or ovular cross-section. The FG-SS method of imaging can account for imperfect positioning of the body part in FOV or non-circular shapes of an organ of interest. Illustration of the anatomy in misalignment with the isocenter is provided in FIG. 20. During a CT image acquisition in this setup 2000, the x-ray source 2001 rotates along a circular path 2002 around a body part 2003 placed between the source 2001 and the detector 2004. Two instances of this rotation, 90 degrees apart from each other, are shown in FIG. 20. If the calculations of the placement of the sheets of the FG drum are based on the distance 2006 between the isocenter 2005 and the outer boundary of the body part, the generated modulated beam will have an overestimated fan angle coverage. An example of an acquired projection that suffers from this misalignment is illustrated in FIG. 21A. If, however, the distances of the sheets 2007 from the center of rotation of the FG drum 2008 are calculated to be unequal in acquisition angles that the object is not aligned with the isocenter, the resulting beam can be modulated such that it corresponds to the positioning of the object. The adjustments of the sheets can continue during a scan, given the robotics outlined in FIG. 11. An example of the corrected projection is illustrated in FIG. 21B. As shown, the projected beam is modulated to match the positioning of the cylinder. Therefore, the chance of saturation in otherwise overexposed regions 2101 is reduced and the x-ray quanta in the most underexposed regions 2102 of the projection is increased. The profiles of a horizontal line 2103 across the two projections are provided in FIG. 21C.

In addition to the imperfect positioning of the body part, the FG-SS adapts for objects with a non-circular cross section. A typical cross section shape is ovular, as is the case for body parts such as the head, chest, or abdomen. The illustration is provided in FIG. 22, outlines the methodology of adjusting the sheets within the FG unit during a scan procedure; the resulting projections are shown in FIGS. 23A and 23B. In the FIG. 22, the gantry setup is depicted at two instances of time—when the setup of the imaging components are 90 degrees apart from each other. The oval-shaped object 2201 is placed between the x-ray source 2202 and the x-ray detector 2203. The length of the major axis 2204 is larger than the length of the minor axis 2205 and consequently, the width of the projection of the object on the detector varies as the source moves along a rotational path 2206. The FG drum 2207 is installed on the gantry and rotates with the source and detector around the object of interest 2201. As shown, the tilting of the FG sheets 2208 can be equally adjusted during a scan such that the width of the formed FG window 2209 varies depending on the gantry angle. With this process, the projected size of the modulated beam is wider in some and narrower in other gantry angular positions.

Figure 22:
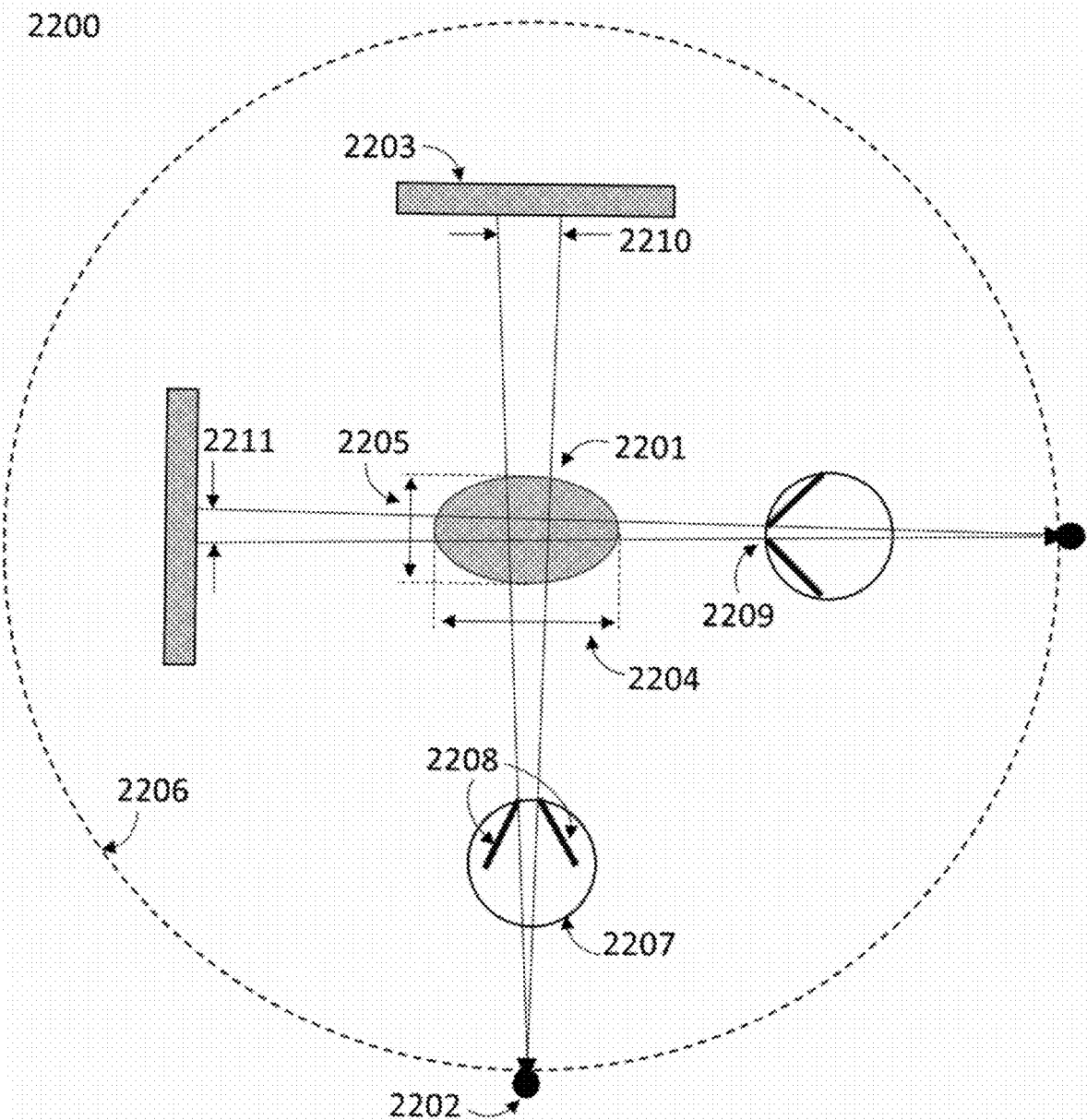
FIG. 22 illustrates the method of imaging an object with elliptical cross section on a CT imaging system equipped with the FG-SS apparatus.

The resulting projections are shown in FIGS. 23A and 23B. Narrowing the FG window, as shown in FIG. 22, results in cutting off the x-ray photons that would otherwise reach the detector at large fan angles. The projection shown in FIG. 23A corresponds to the gantry angular positions where the projection of the elliptical cross section of the object is narrow. As the projections of the cross section gets wider, the size of the FG window increases to accommodate for the broadening of the cross section of the object of interest. FIG. 23B illustrates the resulting projection. The profiles of a line 2103 across the depicted projections are shown in FIG. 23C, highlighting the relatively uniform intensity across the detector columns.

Dose Exposure

Another important metric in assessing the impact of the FG-SS apparatus and method of imaging is the introduced radiation dose to the patient's body. FG-SS can reduce both the inhomogeneity, and the magnitude, of the radiation dose introduced to a body part. Reduction in dose is a direct outcome of modulating the x-ray fluence to match the shape of the organ as the parts of the organ with short beam path receive a reduced number of photons. FIGS. 24A-24C illustrate simulation estimations 2400 of the introduced radiation dose to an average sized breast in a dedicated breast CT system, with and without FG-SS. The coronal and sagittal image segments of the dose image acquired in a system without FG-SS are shown in FIGS. 24A and 24D, respectively. The coronal and sagittal image segments of the dose image acquired in a system with FG-SS are shown in FIGS. 24B and 24E, respectively. The profiles across a horizontal line 2401 in the coronal image segments are shown in FIG. 24C. The profiles across a vertical line 2402 in the sagittal image segments are shown in FIG. 24F. The displayed dose images and the line profiles show a large reduction in the radiation dose introduced to the simulated breast phantom. By utilizing the FG-SS apparatus, an overall reduction of 31% was observed is this case. In addition to the reduction in the magnitude of the dose, the inhomogeneities of the dose distribution are significantly reduced. More specifically and in FIG. 24C, a large dip 2403 is observed in the profile of the dose in the central parts of the breast than its peripheral parts. This is due to the accumulated deposited energy by the uniformly distributed beam in the peripheral regions as the gantry rotates around the breast during a scan. Using FG, however, the dose is targeted more so towards the thickest parts of the breast. This is in general desirable as the signal received from the center of the breast is less than the signal received from its periphery. As a result, a larger portion of the photons are absorbed or scattered due to longer path length and a higher x-ray flux is needed to maintain a similar signal to noise ratio to what is gained from the peripheral regions. Consequently, the dose profile in the system that utilizes the FG becomes homogenized 2404. In addition to making the dose distribution relatively uniform in coronal images, the introduced dose follows the shape of the specific tapering of the breast from the posterior regions towards the nipple. As shown in FIG. 24F, without the FG, the deposited energy increases 2405 towards the anterior anatomy of breast. Utilizing the FG, however, the dose profile 2406 follows the narrowing characteristic of a pendent breast towards the nipple. The combined analysis highlights the benefits of applying the fluence modulation technique outlined in this invention in reducing the overall dose delivered to a patient.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A radiologic computed tomography (CT) system comprising:
   a) a gantry configured to rotate on a first axis of rotation to allow the CT system to capture a plurality of projections of a target;
   b) a x-ray source affixed to the gantry and configured to generate a beam of x-ray photons;

c) a x-ray detector affixed to the gantry;
d) a robotic fluence gate system affixed to the gantry between the x-ray source and the x-ray detector and comprising a rotational platform configured to rotate on a second axis of rotation and a plurality of fluence modulation sheets forming a fluence gate window, the fluence gate system configured to modulate a fluence of the beam of x-ray photons;
e) a robotic scatter shield system affixed to the gantry between the x-ray source and the x-ray detector and comprising a rotational platform configured to rotate on a third axis of rotation and a plurality of scatter shield sheets forming a scatter shield window, the scatter shield system configured to shield scattered x-ray photons from the x-ray detector; and
f) a controller configured to perform at least:
   i) synchronize a speed and a phase of rotation of the gantry, the fluence gate system, and the scatter shield system to maintain a line-of-sight from the x-ray source to the x-ray detector during capture of each projection of the target;
   ii) activate the x-ray source when the line-of-sight is open; and
   iii) deactivate the x-ray source when the line-of-sight is closed.

2. The system of claim 1, wherein one or more of: the x-ray source, the fluence gate system, the x-ray detector, and the scatter shield system are affixed directly to the gantry.

3. The system of claim 1, wherein one or more of: the x-ray source, the fluence gate system, the x-ray detector, and the scatter shield system are affixed indirectly to the gantry.

4. The system of claim 1, wherein the fluence gate system comprises two fluence modulation sheets.

5. The system of claim 1, wherein the fluence modulation sheets comprise an x-ray attention material.

6. The system of claim 1, wherein the fluence modulation sheets are substantially flat.

7. The system of claim 1, wherein the fluence modulation sheets are curved.

8. The system of claim 1, wherein the fluence gate system comprises robotics configured to position each fluence modulation sheet in each of four axes of adjustment to change a size, a shape, or both a size and a shape of the fluence gate window.

9. The system of claim 8, wherein the fluence gate system comprises one or more sensors configured to generate data used to inform the positioning of each fluence modulation sheet.

10. The system of claim 8, wherein the controller is further configured to instruct the robotics of the fluence gate system to position each fluence modulation sheet for each projection of the target.

11. The system of claim 1, wherein the scatter shield system comprises two fluence modulation sheets.

12. The system of claim 1, wherein the scatter shield sheets comprise an x-ray attention material.

13. The system of claim 1, wherein the scatter shield sheets are substantially flat.

14. The system of claim 1, wherein the scatter shield sheets are curved.

15. The system of claim 1, wherein the scatter shield system comprises robotics configured to position each scatter shield sheet in each of four axes of adjustment to change a size, a shape, or both a size and a shape of the scatter shield window.

16. The system of claim 15, wherein the scatter shield system comprises one or more sensors configured to generate data used to inform the positioning of each scatter shield sheet.

17. The system of claim 15, wherein the controller is further configured to instruct the robotics of the scatter shield system to position each scatter shield sheet for each projection of the target.

18. The system of claim 1, wherein the first axis of rotation, the second axis of rotation, and the third axis of rotation are substantially parallel.

19. The system of claim 1, wherein the beam of x-ray photons incident on the x-ray detector is substantially scatter-free.

20. The system of claim 19, wherein the beam of x-ray photons incident on the x-ray detector is scatter-free.

21. The system of claim 1, wherein the target is an anatomical target.

22. The system of claim 21, wherein the beam has a x-ray beam energy falling within a diagnostic range of 20 keV to 140 keV.

23. The system of claim 22, wherein the anatomical target is a human extremity.

24. The system of claim 22, wherein the anatomical target is a human female breast.

25. The system of claim 22, wherein the anatomical target is a whole human body.

26. A radiologic computed tomography (CT) system comprising:
a) a gantry configured to rotate on a first axis of rotation to allow the CT system to capture a plurality of projections of a target;
b) a x-ray source affixed directly or indirectly to the gantry and configured to generate a beam of x-ray photons;
c) a x-ray detector affixed directly or indirectly to the gantry;
d) a robotic fluence gate system affixed directly or indirectly to the gantry between the x-ray source and the x-ray detector and comprising a rotational platform configured to rotate on a second axis of rotation and a plurality of fluence modulation sheets forming a fluence gate window, the fluence gate system configured to modulate a fluence of the beam of x-ray photons; and
e) a controller configured to perform at least:
   i) synchronize a speed and a phase of rotation of the gantry and the fluence gate system to maintain a line-of-sight from the x-ray source to the x-ray detector during capture of each projection of the target;
   ii) activate the x-ray source when the line-of-sight is open; and
   iii) deactivate the x-ray source when the line-of-sight is closed.

27. A radiologic computed tomography (CT) system comprising:
a) a gantry configured to rotate on a first axis of rotation to allow the CT system to capture a plurality of projections of a target;
b) a x-ray source affixed directly or indirectly to the gantry and configured to generate a beam of x-ray photons;
c) a x-ray detector affixed directly or indirectly to the gantry;
d) a robotic scatter shield system affixed directly or indirectly to the gantry between the x-ray source and the x-ray detector and comprising a rotational platform configured to rotate on a second axis of rotation and a plurality of scatter shield sheets forming a scatter shield window, the scatter shield system configured to shield scattered x-ray photons from the x-ray detector; and e) a controller configured to perform at least:
   i) synchronize a speed and a phase of rotation of the gantry, the fluence gate system, and the scatter shield system to maintain a line-of-sight from the x-ray source to the x-ray detector during capture of each projection of the target;
   ii) activate the x-ray source when the line-of-sight is open; and
   iii) deactivate the x-ray source when the line-of-sight is closed.

28. A method of performing radiologic computed tomography (CT) to capture a plurality of projections of a target, the method comprising:
   a) generating, by a x-ray source affixed to a gantry, a beam of x-ray photons;
   b) controlling, by a controller unit, at least the following:
      i) speed and phase of rotation of a robotic fluence gate system affixed to the gantry between the x-ray source and a x-ray detector to maintain a line-of-sight from the x-ray source to the x-ray detector during capture of each projection of the target, the fluence gate system comprising a rotational platform and a plurality of fluence modulation sheets forming a fluence gate window, the fluence gate system configured to modulate a fluence of the beam of x-ray photons;
      ii) speed and phase of rotation of a robotic scatter shield system affixed to the gantry between the x-ray source and the x-ray detector to maintain a line-of-sight from the x-ray source to the x-ray detector during capture of each projection of the target, the scatter shield system comprising a rotational platform and a plurality of scatter shield sheets forming a scatter shield window, the scatter shield system configured to shield scattered x-ray photons from the x-ray detector;
      iii) activation of the x-ray source when the line-of-sight is open; and
      iv) deactivation of the x-ray source when the line-of-sight is closed; and
   c) detecting, by the x-ray detector affixed to the gantry, the beam of x-ray photons.

29. The method of claim 28, wherein the fluence gate system further comprises robotics configured to position each fluence gate sheet in each of four axes of adjustment to change a size, a shape, or both a size and a shape of the fluence gate window and one or more sensors configured to generate data used to inform the positioning of each fluence gate sheet, and wherein the controller is further configured to instruct the robotics of the fluence gate system to position each fluence gate sheet, based at least in part on the data generated by the one or more sensors, for each projection of the target.

30. The method of claim 28, wherein the scatter shield system further comprises robotics configured to position each scatter shield sheet in each of four axes of adjustment to change a size, a shape, or both a size and a shape of the scatter shield window and one or more sensors configured to generate data used to inform the positioning of each scatter shield sheet, and wherein the controller is further configured to instruct the robotics of the scatter shield system to position each scatter shield sheet, based at least in part on the data generated by the one or more sensors, for each projection of the target.

* * * * *

UNITED STATES PATENT AND TRADEMARK OFFICE
CERTIFICATE OF CORRECTION

PATENT NO. : 10,531,844 B1  
APPLICATION NO. : 16/537283  
DATED : January 14, 2020  
INVENTOR(S) : Peymon Mirsaeid Ghazi and Tara Renee Ghazi Page 1 of 1

It is certified that error appears in the above-identified patent and that said Letters Patent is hereby corrected as shown below:

In the Claims

Column 25, Line 37:
Delete "attention" and replace with -- attenuation --.

Column 25, Line 56:
Delete "fluence modulation" and replace with -- scatter shield --.

Column 25, Line 58:
Delete "attention" and replace with -- attenuation --.

Signed and Sealed this  
Twenty-fifth Day of February, 2020

Andrei Iancu  
*Director of the United States Patent and Trademark Office*